US008679789B2

(12) United States Patent
Arnold, Jr. et al.

(10) Patent No.: US 8,679,789 B2
(45) Date of Patent: Mar. 25, 2014

(54) OLIGONUCLEOTIDES COMPRISING A MOLECULAR SWITCH

(75) Inventors: Lyle J. Arnold, Jr., Poway, CA (US); Bob D. Brown, Millington, NJ (US)

(73) Assignee: Gen-Probe Incorporated, San Diego, CA (US)

( * ) Notice: Subject to any disclaimer, the term of this patent is extended or adjusted under 35 U.S.C. 154(b) by 1889 days.

(21) Appl. No.: 10/837,530

(22) Filed: Apr. 30, 2004

(65) Prior Publication Data

US 2005/0042638 A1    Feb. 24, 2005

Related U.S. Application Data

(60) Provisional application No. 60/467,517, filed on May 1, 2003.

(51) Int. Cl.
*C12P 19/34*    (2006.01)
(52) U.S. Cl.
USPC .......................................................... 435/91.2
(58) Field of Classification Search
USPC .......................................................... 435/91.2
See application file for complete search history.

(56) References Cited

U.S. PATENT DOCUMENTS

| | | | |
|---|---|---|---|
| 4,683,194 | A | 7/1987 | Saiki et al. |
| 4,950,613 | A | 8/1990 | Arnold, Jr. et al. |
| 5,223,618 | A | 6/1993 | Cook et al. |
| 5,378,825 | A | 1/1995 | Cook et al. |
| 5,489,677 | A | 2/1996 | Sanghvi et al. |
| 5,539,082 | A | 7/1996 | Nielsen et al. |
| 5,541,307 | A | 7/1996 | Cook et al. |
| 5,723,591 | A | 3/1998 | Livak et al. |
| 5,780,223 | A | 7/1998 | Lupski et al. |
| 5,866,336 | A * | 2/1999 | Nazarenko et al. ............... 435/6 |
| 5,876,930 | A | 3/1999 | Livak et al. |
| 5,925,517 | A | 7/1999 | Tyagi et al. |
| 6,025,130 | A | 2/2000 | Thomas et al. |
| 6,030,787 | A | 2/2000 | Livak et al. |
| 6,103,476 | A | 8/2000 | Tyagi et al. |
| 6,150,097 | A | 11/2000 | Tyagi et al. |
| 6,194,158 | B1 | 2/2001 | Kroes et al. |
| 6,201,107 | B1 | 3/2001 | Lap-Chee et al. |
| 6,239,159 | B1 | 5/2001 | Brown et al. |
| 6,361,940 | B1 | 3/2002 | Van Ness et al. |
| 6,485,903 | B1 | 11/2002 | Mayrand |
| 6,541,617 | B1 | 4/2003 | Bamdad et al. |
| 2001/0055773 | A1 * | 12/2001 | Jayasena et al. ................. 435/6 |
| 2002/0090633 | A1 | 7/2002 | Becker et al. |
| 2003/0165925 | A1 | 9/2003 | Saito et al. |

FOREIGN PATENT DOCUMENTS

| WO | WO 97/46711 | 12/1997 |
|---|---|---|
| WO | WO 99/18238 | 4/1999 |
| WO | WO 99/31276 | 6/1999 |
| WO | WO 00/11446 | 3/2000 |
| WO | WO 03/054223 | 7/2003 |

OTHER PUBLICATIONS

International Search Report for PCT Application No. PCT/US2004/13515.
Bergstrom et al., Synthesis, Structure, and Deoxyribonucleic Acid Sequencing with a Universal Nucleoside: 1-(2'-Deoxy-β-D-ribofuranosyl)-3-nitropyrrole, *J. Am. Chem. Soc.* 117:1201-1209 (1995).
Clegg, Fluorescence Resonance Energy Transfer and Nucleic Acids, *Meth. Enzymol.* 211:353-388 (1992).
Forster, Experimentelle and theoretisch Untersuchung des zwischenmolekularen Übergangs von Elektronenanregungsenergie, *Z. Naturforsch.* A4:321-327 (1949).
Kong et al., Synthesis of oligodeoxyribonucleotides containing degenerate bases and their use as primers in the polymerase chain reaction, *Nucl. Acids Res.* 20:5149-5152 (1992).
Loakes and Brown, 5-Nitroindole as an universal base analogue, *Nucl. Acids Res.* 22:4039-4043 (1994).
Loakes et al., 3-Nitropyrrole and 5-nitroindole as universal bases in primers for DNA sequencing and PCR, Nucl. Acids Res., 23:2361-2366 (1995).
Loakes et al., Stability and Structure of DNA Oligonucleotides Containing Non-specific Base Analogues, J. Mol. Biol. 270:426-435 (1997).
Marras et al., Efficiencies of fluorescence resonance energy transfer and contact-mediated quenching in oligonucleotide probes, Nucl. Acids Res., 30:2-8 (2002).
Nicols et al., A universal nucleoside for use at ambiguous sites in DNA primers, *Nature* 369:492-493, (1994).
Ugozzoli et. al., Fluorescent multicolor multiplex homogenous assay for the simultaneous analysis of the two most common hemochromatosis mutations, *Anal. Biochem* .307:47-53, 2002.
Nutiu and Li, Tripartite molecular beacons. Nucleic Acids Research, 30(18), p. e94(1-9), 2002.
Supplementary European Search Report for EPO Patent Application No. 04751076.3, Oct. 23, 2007.

\* cited by examiner

*Primary Examiner* — Cynthia B Wilder
(74) *Attorney, Agent, or Firm* — Jeffrey E. Landes; Brian S. Sun

(57) ABSTRACT

This invention relates to oligonucleotides comprising a molecular switch which may exist in an "open" or "closed" position. The molecular switch portion of the probe is particularly sensitive to the identity of sequences complementary to the molecular switch. Oligonucleotides containing a molecular switch are applicable to all kinds of hybridization processes. Due to the sensitivity of the switch domain of the oligonucleotide, probes containing a molecular switch are particularly useful in the identification of single point mismatches. More specifically, a portion, but not all, of the oligonucleotide becomes unbound from a mismatched target. The invention further relates to methods of using said oligonucleotides for research reagents, and clinical diagnostics. An exemplary oligonucleotide comprises a first hybridizable domain, a second bridging block domain, and a third binding domain.

36 Claims, 9 Drawing Sheets

The Specimer™ "Molecular Switch" Concept

Match – switch closed

Mismatch – switch open mismatch

= fluorescein label      = black hole quencher

When switch is open fluoresence is quenched

Dual Labeled "Tripartite" Specimer™ Probes Act as Molecular Switches
Example: Fluorescent Labels Modifications are incorporated to produce 5' nuclease resistance.

Replicate Specimer™ Probe reactions against the HFE63D gene.

OLIGONUCLEOTIDES COMPRISING A MOLECULAR SWITCH

FIELD OF THE INVENTION

This invention relates to oligonucleotides used to identify matched or mismatched targets. The invention further relates to methods of using those oligonucleotides for research reagents, and clinical diagnostics.

BACKGROUND OF THE INVENTION

The following discussion of the background of the invention is merely provided to aid the reader in understanding the invention and is not admitted to describe or constitute prior art to the present invention.

The explosion of recent knowledge in basic genetics has spawned numerous clinical follow-up studies that have confirmed an unequivocal association between the presence of specific prevalent genetic alterations and susceptibility to some very common human diseases. In addition, the Human Genome Project's sequencing efforts will contribute yet more candidate disease genes that will require both research-based genetic association studies (to confirm suspected disease links) and, if positive, the translation of these disease-genotype associations to routine diagnostic clinical practice. Given this expanding repertoire of confirmed and reputed disease genes (many for common diseases), the demand for rapid, sensitive, specific, inexpensive assays for their clinical- and/or research-based detection is growing quickly.

As a consequence, clinical genetic testing laboratories, once accustomed to manual, low-volume, high-labor tests on patients with rare, untreatable classic "genetic" diseases, will soon need to develop better high-throughput and semi-automated methods. In the fast-approaching molecular medicine era, these new genotyping methods will be utilized not only for diagnosing symptomatic patients but perhaps, more importantly, for presymptomatically identifying individuals at risk for common, treatable diseases for whom effective preventative interventions may be available.

Oligonucleotide hybridization is a method commonly used in the field of molecular biology for the treatment and diagnosis of disease, as well as the identification, quantitation, and isolation of nucleic acids. Accordingly, it is important to identify methods to increase the specificity and affinity of oligonucleotides for their targets. In this way, diagnostics which provide efficient and precise answers can be made. Various methods for increasing the specificity of oligonucleotides are known in the art, including increasing the length, choosing oligonucleotides that are not likely to cross-hybridize or bind non-specifically and designing oligonucleotides that have a high annealing temperature. (See e.g., Bergstrom et al., *J. Am. Chem. Soc.* 117:1201-1209, 1995; Nicols et al., *Nature* 369:492-493, 1994; Loakes, *Nucl. Acids Res.* 22:4039-4043, 1994; Brown, *Nucl. Acids Res.* 20:5149-5152, 1992).

U.S. Pat. No. 5,780,223 discloses "an improved nucleic acid hybridization process . . . which employs a modified oligonucleotide", wherein "the modified probe contains at least one artificial mismatch". "Suitable natural or non-natural artificial mismatches are, therefore, preferably universal mismatches." U.S. Pat. No. 5,780,223 indicates that when creating more than one artificial mismatch, "a spacing of 10 nucleotides between artificial mismatches is desired". In addition, U.S. Pat. No. 5,780,223 indicates that "artificial mismatch positions account for no more than about 20% of the total number of positions in a probe".

As another example, U.S. Pat. No. 6,361,940 states that the incorporation of a "specificity spacer" that "cannot enter into hydrogen bonding with a base positioned opposite itself in a hybridized complementary base sequence" is capable of "increasing the specificity of a probe nucleic acid for a target nucleic acid". U.S. Pat. No. 6,361,940 indicates that "no two specificity spacers should be adjacent to one another", preferably "separated by 4-14 nucleotides having a wild-type sequence".

SUMMARY OF THE INVENTION

The present invention provides compositions and methods for improving detection of nucleic acid hybridization or non-hybridization. In particular, oligonucleotides containing a "molecular switch" region are provided for use as a hybridization probe or primer. This molecular switch region can be in an "open" (non-hybridized) or "closed" (hybridized) position, while the oligonucleotide as a whole remains in part hybridized to the target sequence (see FIG. 1 schematic). In the open position, the molecular switch can be used to detect the presence of a "mismatch" (i.e, at least one non-hybridizing base pair) between the oligonucleotide and the target sequence. In the closed position, the molecular switch can be used to detect a "match", or a complementary nucleic acid sequence between the oligonucleotide and the target sequence. In certain preferred embodiments, the oligonucleotide remains associated with the target sequence via an "anchor" nucleic acid region that is complementary to a portion of the target nucleic acid. Additional such regions can also be provided in the oligonucleotide if desired. In this manner, other portions of the oligonucleotide are able to "melt" without causing complete "melting" or dissociation of the two strands of the hybrid duplex formed between the oligonucleotide and the target sequence. Alternatively, the design of the molecular switch may cause destabilization of the entire oligonucleotide and affect overall dissociation parameters, such as the melting temperature ($T_m$).

The molecular switch function is provided by a switch domain. This switch domain contains at least two features: (i) a binding domain that contains nucleic acid residues complementary to the target sequence, and (ii) a bridging domain that physically separates the first nucleic acid region that binds to the target sequence from this binding domain. The binding domain is preferably at least 75% complementary in the case of a match to the target sequence; but contains at least one nucleic acid residue that is not complementary for a mismatch (a non-hybridizing base pair). The bridging domain contains non-hybridizing universal, generic or mismatched bases, providing enhanced sensitivity to the presence of a mismatch between the binding region of the switch domain and the target sequence. More than one molecular switch can also be used in a single oligonucleotide or in combination.

Thus, the oligonucleotides containing the molecular switches described herein can be used to improve hybridization methods known in the art that use traditional oligonucleotides. Such methods include, for example, detection of nucleic acid polymorphisms (such as SNPs—single nucleotide polymorphisms), various polymerase chain reactions (PCR) (such as quantitative PCR, end-point PCR, real-time PCR), nuclease protection assays, expression assays, and T7 or SP6 amplification reactions.

According to a first aspect of the present invention there is provided an oligonucleotide comprising two general regions. The first region of the oligonucleotide is a nucleic acid region that is complementary to some portion of a target nucleic acid. This region serves to "anchor" the oligonucleotide to the target nucleic acid by forming a stable duplex. The term "complementary" as used herein, means that base pairs are held to a target nucleic acid by hydrogen bonding interactions in the form of Watson-Crick base pairing or other hydrogen bonding interactions including Hoogsteen and reverse Hoogsteen hydrogen bonding, wherein at least 90% of said base pairs form hydrogen bonding interactions with nucleotides or analogues thereof in the target sequence. This anchor region may be about 15-10,000 nucleotides in length, preferably about 30-200 nucleotides, more preferably about 15-150 nucleotides.

The second region is the switch domain, containing a bridging domain and a binding domain. The binding domain contains nucleic acid sequence allowing it to bind a second portion of the same target nucleic acid. The binding domain optimally hybridizes with higher affinity to the target nucleic acid than the bridging domain. Preferably, the nucleic acid sequence of the binding domain is greater than 75% homologous to the target nucleic acid, more preferably greater than 80%. In the case of an exact match between the binding domain and this second portion of the target nucleic acid, this sequence would be fully complementary. As used herein, the term "fully complementary" refers to a 100% base pair match between two nucleic acid sequences, where every base pair hybridizes under appropriate conditions. Preferably, the binding domain consists of 2-20 nucleic acid bases or analogues thereof where each forms a Watson-Crick hydrogen bonds with a matched target.

The bridging domain preferably includes universal bases, natural bases or analogues thereof that do not form Watson-Crick hydrogen bonds (non-hybridizing) with the target sequence under conditions where the oligonucleotide forms a stable double-stranded duplex with a target nucleic acid, e.g., via the first complementary region. Universal bases, as used herein are ribo and deoxyribo base analogues that are capable of hydrophobic stacking, but do not form Watson-Crick, Hoogsteen or reverse Hoogsteen, or related hydrogen bonds with nucleotides or analogues thereof comprising target nucleic acid sequences. Examples include, but are not limited to 5-nitroindole deoxyriboside, 3-nitropyrrole deoxyriboside, nedularin, and the like. Preferably, the bridging domain is 2-20 nucleotides in length (as used herein the "-" indicates that the range includes each of the integers 2, 3, 4, 5, . . . 18, 19, and 20 inclusive, but is shortened herein for convenience, this "-" should be taken as literally expressing each of those integers herein and providing each of the possible combinations of numbers). In alternative embodiments, the bridging domain may contain a minimal number of hybridizing bases (preferably less than a total of 5 hybridizing bases) as long as the overall bridging domain has weak hybridization properties.

The switch domain is able to discriminate between (i) nucleic acid residues of a target nucleic acid that are complementary to said binding domain (a "match"), and (ii) nucleic acid residues of a target nucleic acid that contains at least one nucleic acid residue that is not complementary to the binding domain (a "mismatch"); under conditions wherein the first region of the oligonucleotide forms a stable duplex with the target nucleic acid.

Optionally, the switch domain may also contain an internal binding sequence of about 1-15 nucleotides capable of binding to an internal position of the oligonucleotide to form a short loop structure. With the internal binding sequence, this binding will normally take the form of Watson-Crick hydrogen bonding. In a preferred embodiment, this internal binding sequence positions detectable labels adjacent to each other to amplify the effects when the switch is in an open position.

Additionally, the internal binding sequence can serve to reduce the stability of the complementary portion of the oligonucleotide for the target nucleic acid when the switch is in an open position. Preferably, the internal binding sequence serves to position a fluorescent molecule adjacent to a quenching molecule to more fully quench fluorescence when the switch is in an open position. The open position of the switch may be due to interaction of the oligonucleotide with an unmatched target or may be due to the oligonucleotide existing in an unhybridized form.

In a certain embodiment where the oligonucleotide may be used as a primer in an enzymatic reaction, the switch domain is positioned on the 3' terminus. In this embodiment, the oligonucleotide does not support 3' extension in the presence of a mismatch target, but does support extension with a matched target. A "primer", as used herein, refers to an oligonucleotide that can be extended by adding nucleotides in the 3' direction when it is hybridized to a single-stranded DNA or RNA template.

Thus, the term "oligonucleotide", as used herein, includes a polymer of naturally occurring nucleic acid bases, as well as a polymer having analogues of nucleic acids, and derivatives thereof including universal bases. Preferably invention oligonucleotides are at least 10-200 bases in length, but may be longer depending on the nature of the target nucleic acid and the method used to synthesize the oligonucleotide. Oligonucleotides may also include other components, such as polyA or polyT tails, and the like, as desired by the user.

The target nucleic acid may be any DNA or RNA, mixed DNA and RNA sequences or analogues thereof, in single-stranded or double-stranded form (or duplex) form, to which at least a portion of the oligonucleotide binds through Watson-Crick base pairing or other hydrogen bonding interactions including Hoogsteen and reverse Hoogsteen base pairing. Such binding will generally be specific to allow detection of the target by the oligonucleotide under appropriate environmental conditions. Such specificity can be tailored by standard procedure to suit the expected mixture of other nucleic acids that may be present with the target nucleic acid. For example, in certain situations it will be preferable to have absolute specificity where the oligonucleotide recognizes and binds only one type of nucleic acid; in other situations where the number of competing nucleic acids is limited, the specificity can be reduced. Those in the art are fully aware of such choices in the different situations. A "double-stranded" or duplex" form, as used herein, means a linear array of two single-stranded nucleic acids or analogues thereof held together by hydrogen bonding interactions.

As used herein, "discriminate" with reference to the switch domain, means that the switch domain is able to detect and/or quantify the presence of a matched target as compared to an unmatched target, or to alter its structure in the presence of a matched or unmatched target.

Typical hybridization conditions are known to one of skill in the art, and variations of salt, temperature, pH, and the presence of other agents in a buffer solution may be developed to allow for the formation of a duplex between the oligonucleotide and complementary target nucleic acid region, especially between the first complementary region of the oligonucleotide that anchors to the target nucleic acid.

In a preferred embodiment, the oligonucleotide contains at least one detectable label, preferably a fluorescent label. As used herein, a "detectable label" is a chemical moiety that can be detected using optical, chemical, biochemical, magnetic, electronic, or electromagnetic means. Detectable labels include ligand binding species such as biotin; chemiluminescent agents such as acridinium esters, electron transport substances such as daunomycin and methylene blue; fluorescent compounds, compounds that change the fluorescence of other compounds such as quenchers; compounds that absorb light energy and transfer the energy to other substances such as absorbers; and the like.

Typically, the amount of signal detected from a detectable label is capable of being readily quantified, e.g., quantity of fluorescence emitted. In further preferred embodiments, the amount of signal detected from a detectable label of the oligonucleotide is determinative of the hybridization status of the switch domain. The "hybridization status", as used herein, refers to whether the switch domain is open (mismatch, single-stranded oligonucleotide region) or closed (match, oligonucleotide region is double-stranded with target nucleic acid). The amount of signal is determinative of the hybridization status when, under appropriate environmental conditions where the region is duplexed with the target, the label will provide a mechanism to determine whether or not the switch domain is in proximity to either a matched or unmatched target. Preferably, the amount of signal detected from the detectable label is decreased with the switch domain is not hybridized to the target nucleic acid (mismatch). This decrease is relative to the amount of signal detected from the detectable label when the switch domain is hybridized to the target nucleic acid (match).

Alternatively, a fluorescent label may change its fluorescent properties in response to the amount of duplex formed by the switch domain. A "change in fluorescent properties", as used herein, includes, for example, a change in either the amount of fluorescence or the wavelength of the fluorescence. Examples of an increase of fluorescence when associated with duplexes are ethidium bromide and its analogs, SYBER Green, SYBER Gold, and the like. The fluorescent label may also undergo a ligand exchange reaction in response to changes in the switch position of the oligonucleotide. A "ligand exchange", as used herein, means the replacement of one ligand for another in a chelation complex. Of particular interest are lanthamide fluorescent complexes whose degree of fluorescence is highly dependent on the ligands in its chelation complex. Also of particular interest are constructions that upon opening of the switch the lanthamide comes into contact with a ligand that "poisons" fluorescence and thus gives a fluorescent signal only when the switch is closed.

In an alternative preferred embodiment, the oligonucleotide contains both a fluorescent label and a quencher moiety. A "quencher", as used herein, is a moiety that interacts with the fluorescent label to modulate the amount of signal detected from the fluorescent label. Typically, the quencher moiety decreases the amount of signal emitted by the fluorescent label when it is close physical proximity to the fluorescent label. Thus, in the open position, the unmatched region of the oligonucleotide is able to come into physical proximity to the fluorescent label and quench it; while in the closed position, this region is duplexed with the target nucleic acid and is physically separated from the fluorescent label, and no quenching effect is possible.

In another alternative embodiment, the oligonucleotide contains two fluorescent labels and a quencher moiety. In this case, the first fluorescent label, together with the quencher, is determinative of the hybridization status of the switch domain as above. In addition, the second fluorescent label is determinative of the hybridization status of the anchor region of the oligonucleotide to the target nucleic acid sequence. This second label provides a monitor of the hybridization of the whole oligonucleotide, as an internal control for the amount of duplex that forms with the target oligonucleotide sequence. This can then be compared to the amount of signal detected from the first label to provide a quantitation of the degree of mismatch as well, or the relative portions of matched and unmatched target sequences.

In yet another alternative embodiment, the oligonucleotide contains two fluorescent labels. These two fluorescent labels may then interact to modulate the amount of signal detected from either or both labels, dependent on the hybridization status of the switch domain. For example, the first fluorescent label may serve as an absorber while the second fluorescent label may serve as an emitter, and this interaction may take place only when the molecular switch is in its open position.

In another embodiment, the oligonucleotide may contain a modification of 5' end of the sequence that makes the oligonucleotide resistant to digestion by enzymes possessing 5' nuclease activity. As used herein, this modification is achieved by synthesizing the oligonucleotide to make it resistant to cleavage of the phosphodiester linkages of the 5' portion of the oligonucleotide by enzymes with 5' exonuclease activity. Modifications to impart such resistance may include, but are not limited to, ribonucleotides, 2'OMe ribonuclesides, phosphothioate internucleotide linkages, phosphodithioate internucleotide linkages, methylphosphonate internucleotide linkages, PNA derivatives, morpholino derivatives, LNA (locked nucleic acid) derivatives, and internucleotide linkages with a 5'-5' linkages, terminal 5'-thiophosphate groups, and terminal 5'-alkylthiophosphate groups.

As used herein, the phrase "resistant to digestion" means that the oligonucleotide, compared to native RNA or DNA equivalent is more resistant to digestion by enzymes that are capable of digesting oligonucleotides at their 5' ends, particularly when the oligonucleotides are hybridized to target nucleic acid sequences. For example, one could confer resistance to digestion by DNA or Taq polymerase, possessing 5' exonuclease activity when it encounters a duplex along a single stranded DNA template. In this example, the DNA polymerase would attempt to cleave an oligonucleotide that it encounters, starting from its 5' end (see FIG. 2 schematic). Where the oligonucleotide is left unmodified, the sensitivity to digestion by such enzymes is preserved.

In another embodiment, the oligonucleotide may be attached to an electron conducting solid surface, where the amount of matched target controls the amount of current flow. In such embodiments, the detectable label is a single electron conductor. As used herein, the phrase "single electron conductor" refers to moieties that can accept and transfer single electrons to other chemical species. Examples include hydroquinones such as daunomycin. The species capable of accepting a single electron accepts electrons from a duplex, and transfers these electrons to other species in solution. It is not required that this species be covalently attached to the oligonucleotide. For example, it may associate by hydrophobic or other interactions with the duplex. A non-limiting example is methylene blue, that is capable of binding near the ends of duplexes (and is not covalently attached) and transferring single electrons into solution to, for example ferricyanide to give a color change upon reduction of the ferricyanide.

According to a second aspect of the present invention there is provided an oligonucleotide comprising the same framework regions as described above, except that these regions are capable of binding to a double-stranded target nucleic acid. Using this invention oligonucleotide, the first complementary anchor region of the oligonucleotide thus forms a stable triple-stranded nucleic acid with the target nucleic acid. The switch domain is able to discriminate between double-stranded target nucleic acid that is complementary to the binding domain and double-stranded target nucleic acid that contains at least one nucleic acid residue that is not complementary to the binding domain.

The first region of this single-stranded oligonucleotide is complementary to a sequence of nucleic acid residues of a double-stranded target nucleic acid, thus forming a stable triple-stranded complex. Recognition can be through Hoogsteen, reverse Hoogsteen, or parallel recognition where the third strand, in this case the oligonucleotide, is in the same orientation and has the same sequence as one of the Watson-Crick duplex strands of the target duplex strand. The triple-stranded structure is typically formed when two strands are hybridized to each other by conventional base pairs, and a third strand associates with the duplex through one or both strands by one of a number of hydrogen bonding interactions. These include recognitions of underlying purine sequences of one of the strands using Hoogsteen or reverse Hoogsteen hydrogen bonding interactions. In another mode, a third strand binds in the major groove formed between an underlying Watson-Crick hydrogen bonded duplex, by binding in the major groove formed by the underlying Watson-Crick duplex.

According to a third aspect of the present invention there is provided a tandem oligonucleotide assembly comprising at least two oligonucleotides containing molecular switches as described above, wherein these oligonucleotides are positioned in tandem. The term "tandem oligonucleotide assembly", as used herein, means that at least two oligonucleotides are used for hybridization such that they become positioned side-by-side when hybridized to a target nucleic acid sequence. In one embodiment, the oligonucleotides may be positioned side-by-side such that there are no unhybridized target nucleotides in the target nucleic acid sequence between the oligonucleotides. Alternatively, there may be a space of 1-10 unhybridized nucleotides in the target nucleic acid sequence separating the oligonucleotides. In certain embodiments, one oligonucleotide of the tandem oligonucleotide assembly may be attached to a solid support, such as a glass, plastic or metal surface.

In a preferred embodiment, this invention tandem oligonucleotide assembly contains a detectable label associated with each oligonucleotide. When this tandem oligonucleotide assembly is hybridized to a target nucleic acid, the amount of signal detected from either or both detectable label(s) is altered, relative to the amount of signal detected from either label when either oligonucleotide is hybridized to the target nucleic acid individually. Preferably, the separate detectable labels are both fluorescent labels, where the first fluorescent label transfers energy non-radiatively to the second fluorescent label when both oligonucleotides are hybridized to the target nucleic acid.

In another embodiment, the tandem oligonucleotide assembly contains two binding domains (in the switch domains of two respective oligonucleotide components) that are capable of hybridizing, at least in part, with overlapping regions of the target nucleic acid. In this embodiment, the switch domains each have the potential to hybridize to a portion of the same target nucleic acid sequence in the vicinity of each of said switch domains. Overlapping switch domains are designed to further increase the specificity of discriminating matched and unmatched target sequences. They are preferably designed so that the target sequence forms a matched target with the switch domain of a first adjacent oligonucleotide, and the target sequence forms an unmatched target with the switch domain of the second adjacent oligonucleotide. In this way the switch domains of said first and second adjacent oligonucleotides compete with each other for forming a stable duplex with the target nucleic acid. Furthermore, the switch domain of first adjacent oligonucleotide that binds an unmatched target nucleic acid sequence is held in a more fully "open" position, since the target nucleic acid sequence more preferably forms a stable duplex with the switch domain of the second adjacent oligonucleotide that forms a match with the target nucleic acid sequence.

In one embodiment, each of the adjacent oligonucleotides contains a fluorescent label and a quenching label such that when the switch domain is associated with an unmatched target the quencher reduces the fluorescence intensity of the fluorescent label. In another embodiment, the first adjacent oligonucleotide contains a first fluorescent label and the second adjacent oligonucleotide contains a second fluorescent label such that when the switch domain of the first adjacent oligonucleotide is associated with a matched target, fluorescent energy transfer between said first label and said second label is enhanced, and when the switch domain of the second adjacent oligonucleotide is associated with a matched target the fluorescent energy transfer between said first and second labels is reduced.

In another embodiment, each of the adjacent oligonucleotides contain chemiluminescent labels, preferably two separately detectable acridinium esters. These two acridinium esters may be detected due to differing physical properties. One example is the use of chemiluminescent acridinium esters with differing rates of photo emission. These have been referred to as "flashers" and "glowers". The differing rates of photo-emission allow the proportions of an intact "flasher" and "glower" to be readily determined. Alternatively, the wavelength of light emitted by two different chemiluminescent acridinium esters can be used to resolve the proportions of intact label present in a reaction medium.

In a fourth aspect of the present invention there is provided a method for determining in a sample the amount of target sequence that is complementary to the binding domain of the oligonucleotide. Invention methods comprise contacting the oligonucleotide containing a molecular switch as described above with a sample putatively containing target nucleic acid under conditions suitable for hybridization. The hybridization status of the switch domain is then determined as a measure of the amount of target nucleic acid sequence in said sample that is complementary to the binding domain of the switch domain.

Such invention methods include the use of invention oligonucleotides in a quantitative PCR assay, where the amount of a matched target sequence is determined during the PCR amplification reaction; or an end-point PCR assay, where the amount of a matched target sequence is determined after the completion of the PCR amplification reaction. Invention methods also include the use of invention oligonucleotides in real-time T7 or SP6 amplification reactions. T7 and SP6 refer to bacterial promoters that have been used to amplify target nucleic acid sequences by first forming a DNA duplex with the promoter inserted into the duplex. The product of the amplification is a single stranded RNA, so typically the oligonucleotides of this invention would be used to detect single stranded RNA as it was produced by the amplification process. This type of reaction may also be monitored real-time or at the end-point as for the PCR reactions described above.

In a fifth aspect of the present invention there is provided a method for determining in a sample the amount of target sequence that is complementary to the binding domain of the first oligonucleotide of an invention tandem oligonucleotide assembly where two oligonucleotide in tandem both contain fluorescent labels, and the amount of target sequence that is complementary to the binding domain of the second oligonucleotide of the tandem oligonucleotide assembly. These invention methods comprise contacting the tandem oligonucleotide assembly with a sample putatively containing the target nucleic acid under conditions suitable for hybridization. Energy transfer from the first fluorescent label to the second fluorescent label is then measured to determine the hybridization status of each switch domain.

BRIEF DESCRIPTION OF THE DRAWINGS

FIGS. 4A-4D represent probes X2WtH63D (SEQ ID NO:2), X5WtH63D (SEQ ID NO:5), X4WtH63D (SEQ ID NO:4) and X8WtH63D (SEQ ID NO:8) respectively; and targets AntH63DWt (SEQ ID NO:13) and AntH63DMu (SEQ ID NO:18).

FIGS. 5A-5D represent probes X3WtH63D (SEQ ID NO:3), X10WtH63D (SEQ ID NO:10), X9WtH63D (SEQ ID NO:9) and X6WtH63D (SEQ ID NO:6) respectively; and targets AntH63DWt (SEQ ID NO:13) and AntH63DMu (SEQ ID NO:18).

FIGS. 6A-6B represent probes X14WtH63D (SEQ ID NO:14) and X11WtH63D (SEQ ID NO:11) respectively; and targets AntH63DWtLong (SEQ ID NO:19) and AntH63DMuLong (SEQ ID NO:20).

DETAILED DESCRIPTION OF THE INVENTION

Figure 1:
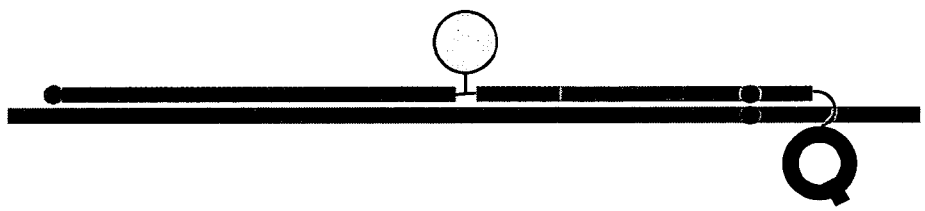
FIG. 1 is a schematic illustration of the Specimer™ "Molecular Switch" concept of the present invention.
Figure 1:
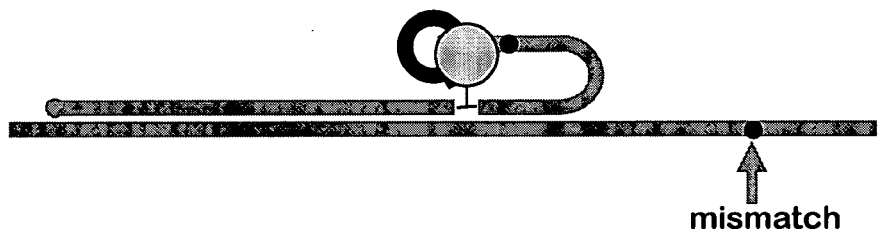
Figure 1:
Figure 1:
Figure 2:
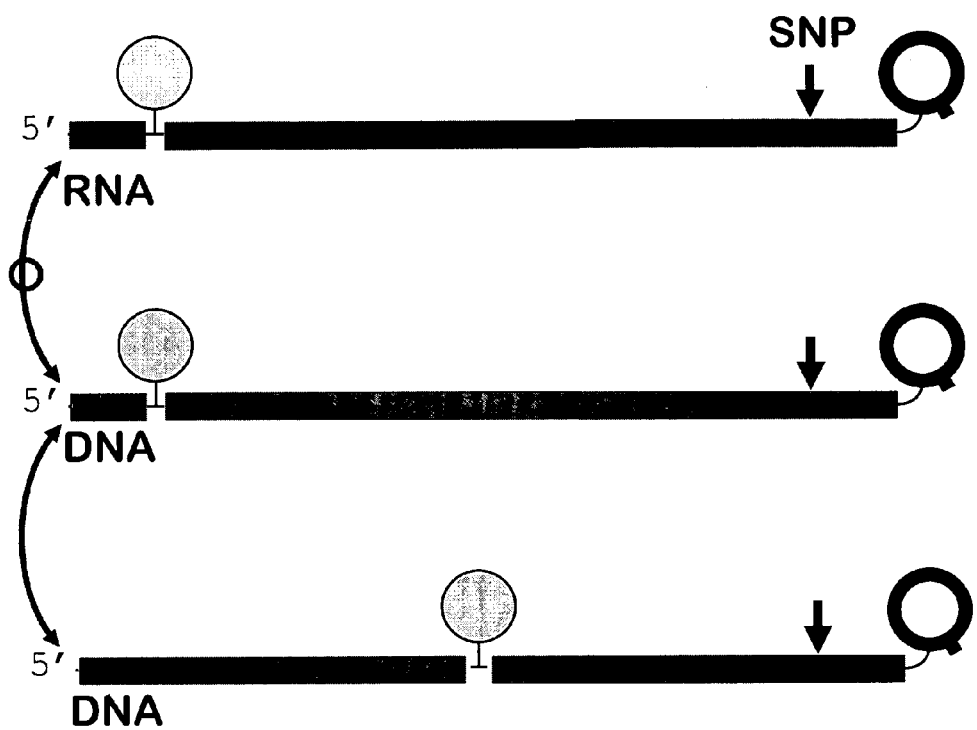
FIG. 2 is a schematic illustration of one embodiment of the present invention wherein dual labeled "tripartite" Specimer™ probes acts as molecular switches.

Disclosed herein is the use of universal bases, natural bases or analogues thereof to produce a "molecular switch" wherein the "molecular switch" produces a sub-domain in a hybridization probe or primer, which has enhanced sensitivity to the presence of a mismatch. In this way the "molecular switch" portion of the probe or primer can "open" or "closed" without requiring that the entire probe or primer become dissociated from the nucleic acid target to which it is hybridized. As shown herein, when the "molecular switch" is combined with detection methods sensitive to the switch being in an "open" or "closed" position, the ability to detect small changes in the sequence of the target sequence is amplified. As shown herein, the incorporation of a molecular switch comprising universal bases in an oligonucleotide amplifies the differentiation of nucleic acids that differ by as little as a single nucleotide. In fact, as shown in the working examples provided herein, the presence of an exemplary "molecular switch" construct comprising 4-6 universal base and 5-8 hydrogen bonding natural bases was able to identify a single mismatch over a range of 35° C. In comparison, oligonucleotides containing all natural bases give an effect of only 3-5° C. The oligonucleotides disclosed herein were found to be very specific. By "target" is meant a nucleic acid sequence to be detected, quantified, or amplified, etc., consisting of either DNA or RNA or analogues thereof, amplified or unamplified and single-stranded or duplex.

It is further disclosed herein that the presence of a molecular switch very significantly increases the ability to detect even single mismatches, for example Single Nucleotide Polymorphisms (SNPs). In one preferred embodiment, oligonucleotides are designed to contain separate domains comprising sequentially along their length a first hybridizing "complementary region", a second non-hybridizing domain or partially non-hybridizing domain, referred to here as a "bridging domain", and a third hybridizing domain referred to here as a "binding domain", wherein the complementary and binding domains are specific for the sequence which is to be identified. Further the "binding domain" has less affinity for the target sequence than corresponding "complementary region". The switch domain of the oligonucleotide, probe, or primer comprises a "bridging domain" and a "binding domain", so that in their simplest form such oligonucleotides, probes, and primers consist of a complementary region and a switch domain. In a further embodiment, the SNP or polymorphism to be detected is located within the "binding domain" of the switch domain and has less affinity for its corresponding target sequence than the complementary region for its target sequence. In this manner, portions of the oligonucleotides comprising probes and primers are able to "melt" without causing complete "melting" or dissociation of the entire hybrid duplex formed between the oligonucleotide and its corresponding target nucleic acid sequence. Alternatively, the presence of the switch domain may alter the stability of the entire oligonucleotide, for example, affecting the melting temperature ($T_m$) of the oligonucleotide. Under such circumstances, when the switch is in the open position, the entire oligonucleotide becomes destabilized. In contrast, a "weak" switch domain in the open position would minimally affect the stability of the entire oligonucleotide (i.e., $T_m$ remains constant).

While in one mode, oligonucleotides have a "tripartite" construction, they may also be comprised of four, five, or even more sub-domains, as long as the above three domains are included. Additionally, the switch domain of the oligonucleotide need not be restricted to one or the other end of the oligonucleotide. Oligonucleotides may also be constructed such that the switch domain is designed into the interior portion of the oligonucleotide. In general the switch domain of the oligonucleotide contains a "bridging domain" comprising 2-11 universal, generic, or mismatched natural bases and a "binding domain" that forms standard Watson-Crick duplex interactions. Detection systems which may be used are able to identify whether a portion of the probe is "open" or "closed". Detection systems capable of this include, but are not limited to: fluorescent, chemiluminescent, electron conduction, calorimetric, etc. Additionally, the "open" or "closed" position of the switch can be coupled to enzyme systems that act either on the "open" or "closed" form of the switch in a differential manner.

Additionally, due to the fact that molecular switch can be used as sensors by being in an "open" versus "closed" position in response to very subtle changes in the target nucleic acid region in the vicinity of the switch, many different formats become possible using molecular switch oligonucleotides. In the course of characterizing molecular switch oligonucleotides, it is also disclosed herein that the switch may be designed to have or not to have an overall destabilizing effect on the oligonucleotide for a nucleic acid target sequence. The precise structure of the molecule switch had two primary effects. First, the ease with which the switch was able to occupy an "open" or "closed" position in response to an unmatched target sequence could be easily controlled by the number and type of nucleotides in the "binding domain". Second, depending on the stability of binding domain of the switch domain with matched nucleic acid targets, the switch domain of the oligonucleotide can contribute added stability to the oligonucleotide for a matched target sequence compared to a mismatched target sequence. As a result, not only does the switch domain "close" and "open" in response to matched and mismatched targets respectively, it can also contribute to a decrease in the affinity of the oligonucleotide for the target when "open" compared to an increase in affinity of the oligonucleotide for the target when "closed". Increases and decreases in affinity of the oligonucleotide for the target are readily observed by changes in the $T_m$ of melting of duplexes formed between the oligonucleotide and the target. Alternatively, the switch domain can be constructed so that it does not significantly contribute to the stability of the oligonucleotide, while still being highly responsive to the presence of matched compared to mismatch targets. Under the condition where the switch domain contributes little or no stability to the oligonucleotide for the target, the discrimination of matched and mismatched targets is governed exclusively by the "open" versus "closed" position of the "molecular switch".

Due the fact that the switch domains of oligonucleotides can be constructed to have their own hybridization properties, a large number of assay formats can be used in ways not previously possible. For example, tandem oligonucleotide can be used where switch domains are constructed on the 5' end of one of the tandem oligonucleotides and in a 3' position on the end of the other tandem oligonucleotide such that the two switch regions are oriented towards each other when the two tandem oligonucleotides hybridize to a common target sequence. Furthermore, detectable labels can be incorporated into or near the ends, of the two switch domains to provide a unique signal only when the two switch domains are associated with target sequences. Examples of detectable are labels that are active through the process of fluorescent resonance energy transfer. This can provide a method of very precise discrimination of matched verses mismatched targets. In addition, the individual oligonucleotide may contain quenching moieties that reduce the fluorescent background when the individual tandem oligonucleotides are unhybridized. This provides ideal utility where background associated with unhybridized probes needs to be very low, for both diagnostic and in-vivo and in-situ assay formats.

Additionally, adjacent oligonucleotides for hybridization to a target sequence can be constructed where the switch domains of each of the oligonucleotides overlap in there possible hybridization for a target sequence. The switch domains can additionally be constructed so that one switch "closes" in the presence of one target sequence, and the other switch "closes" in response to a different target sequence. In this way the switches compete with each other to even more positively identify target sequences since when one switch is "closed" the other is held more completely "open". Still further the switch domains of the tandem probes can be labeled with different detectable labels that provide a determination of which of the switch domains is in an "open" position. In addition, the switch domains compete for hybridization for a target sequence where, depending upon the matched verses mismatched status of the target, one switch is "open" and the other is "closed".

In yet another application of this invention long oligonucleotides containing 30-200 hydrogen bonding nucleotides can be combined with a molecular switch. Oligonucleotides of this kind of structure can form very stable duplexes with target sequences and can enable the oligonucleotides to invade and overcome problems associated with the folded secondary structure of target nucleic acids, and at the same time, still allow the oligonucleotide to detect very small differences between matched and mismatched target sequences owing to the target discriminating properties of the switch domain of the oligonucleotide.

In a still further embodiment, a short section of 2-8 nucleotides may be attached to the binding domain to produce a "clamp domain". The purpose of the "clamp domain" is to orient one label adjacent to another label when the binding domain is "open". A preferred embodiment is to further orient a fluorescent label next to a quencher, such that fluorescence due to the fluorescent label is more completely quenched in the switch "open" position. This mode of the invention has an additional benefit in that upon binding of internal bases by the clamp domain the complementary region of the oligonucleotide looses affinity for the target sequence due to a portion of the base pairs of complementary region becoming associated with the clamp domain.

Oligonucleotides

Thus, various embodiments of the oligonucleotides contain universal and/or other unnatural bases and/or natural bases that form a "bridging domain" as part of a switch domain and methods of using such oligonucleotides as reagents, primers and probes to diagnose and treat various diseases. Embodiments of the oligonucleotides which can be constructed to be used for this purpose can be found in the U.S. patent application Ser. No. 09/931,732, filed Aug. 16, 2001; Ser. No. 09/932,129, filed Aug. 16, 2001; Ser. No. 09/136,080, filed Aug. 18, 1998; and Ser. No. 10/142,729, filed May 8, 2002; all of which are herein incorporated by reference in their entirety.

In some contexts, the term "universal base" is used to describe a moiety that may be substituted for any nucleic acid base. The universal base need not contribute to hybridization, but should not significantly detract from hybridization. Universal bases include, but are not limited to, 2-deoxyinosine, 2-deoxynebularine, derivatives of natural nucleotides such as isocytidine, isothymidine and isoguanine, and ribo and deoxyribo derivatives of 5-nitroindole and 3-nitropyrrole. In some embodiments, these universal, analogues of natural bases, or natural bases are juxtaposed to form a single "bridging domain". Desirably, at least 2, 3, 4, 5, 6, 7, 8, 9, 10, or 11 universal bases, natural bases or analogues of natural bases are juxtaposed in the "bridging domain" and an oligonucleotide may contain 1, 2, 3, 4, 5, 6, or 7, "bridging domains" depending on the length of the oligonucleotide and the desired effect. Further, some embodiments contain a non-nucleic acid linker such as a spacer 9, spacer 18, spacer C3, or an abasic spacer such as dSpacer so as to provide greater flexibility in the molecule.

Additionally, the oligonucleotide may contain internal or terminal linker-arm sites to enable attachment of desired labels at specific locations. These linker-arms may be attached to an nucleic acid base or backbone such as a 5-allyl substitution on thymidine, or they may be inserted into the sequence as a non-nucleotide linker-arm such as a C7 Unilinker (Clontech). Alternatively, labels may be positioned at desired locations in the oligonucleotide by incorporating the label as a synthon appropriate to the DNA synthesis conditions being used. For direct incorporation of the label during DNA synthesis, the label may be attached to a nucleic acid base, or provided as its own synthon devoid of a nucleotide component and inserted internally into the oligonucleotide sequence or attached at a 3' or 5' terminal position of the oligonucleotide. Another way to incorporate labels is to have them attached to the solid support used for DNA synthesis such that upon initiation of the DNA synthesis the label becomes incorporated into the synthetic oligonucleotide. Such labeling methods are well known in the art.

It is further contemplated that unnatural bases can be substituted for a natural base within the oligonucleotide to modify the affinity of the oligonucleotide, particularly in the region of the "binding domain". Typically a higher affinity for a specific hydrogen bonding nucleotide is desired, but a lower affinity may also be used. These kinds of modifications increases the ability to differentiate a single nucleotide polymorphism or a polymorphic site from a normal site. It is particularly desirable to incorporate such unnatural bases in the "binding domain" of the switch domain to further aid in the discrimination of mismatches.

Embodiments include oligonucleotides having at least 10% universal, non-hydrogen bonding natural bases or analogues thereof or a mixture of universal and non-hydrogen bonding natural bases or analogues thereof. Other embodiments include oligonucleotides having at least 11%, 12%, 15%, 20% or 30% universal, generic or a mixture of universal and generic bases. Still more embodiments are oligonucleotides with at least 21%, 22%, 23%, 24%, 25%, 26%, 27%, 28%, 29%, 30%, 35%, 40%, 45%, 50%, or more universal, non-hydrogen bonding natural bases or analogues thereof or a mixture of universal and non-hydrogen bonding natural bases or analogues thereof and unnatural bases located at the SNP position to enhance discrimination.

In one embodiment, universal bases include, but are not limited to, 2-deoxyinosine, 2-deoxynebularine, derivatives of natural nucleotides such as iso-cytidine, iso-thymidine and isoguanine, and ribo and deoxyribo derivatives of 5-nitroindole and 3-nitropyrrole. In some aspects, these universal, non-hydrogen bonding natural bases or analogues thereof or mixtures of universal and non-hydrogen bonding natural bases or analogues thereof are juxtaposed. Desirably, at least two, three, four, five, six, seven, or eight universal, non-hydrogen bonding natural bases or analogues thereof or a mixture of universal and non-hydrogen bonding natural bases or analogues thereof are juxtaposed.

In some aspects, it may also be desirable to combine universal, non-hydrogen bonding natural bases, hydrogen bonding bases, and analogues thereof to produce the "bridging domain" of the oligonucleotide. The oligonucleotides described herein may also contain natural bases or unnatural base analogs that hydrogen bond to natural bases in the target nucleic acid. Additionally, the oligonucleotides described herein may contain natural bases or unnatural base analogs or other modifications that have a lower or higher affinity to or ability to hydrogen bond to natural bases, relative to any natural base. By "non-naturally occurring base" is meant a base other than A, C, G, T and U, and includes degenerate and universal bases as well as moieties capable of binding specifically to a natural base or to a non-naturally occurring base. Non-naturally occurring bases include, but are not limited to, propynylcytosine, propynyluridine, diaminopurine, 5-methylcytosine, 7-deazaadenosine iso-guanine, iso-cytosine, iso-thymidine, and 7-deazaguanine. Embodiments include oligonucleotides having universal, non-hydrogen bonding natural bases or analogues thereof or a mixture of universal and non-hydrogen bonding natural bases or analogues thereof which are juxtaposed. In one embodiment, the number of juxtaposed bases is 2 or more. In one embodiment, the number of juxtaposed bases is 4 or more, including but not limited to, 5 or more, 6 or more, 7 or more, and 8 or more. The juxtaposed bases may substitute for any natural base and may substitute for a variety of different natural bases. The juxtaposed bases may be as close as 1 nucleotide from a mismatch. Another embodiment concerns a method of increasing the specificity of an oligonucleotide by substituting at least 4 juxtaposed nucleic acids with universal or non-hydrogen bonding natural bases or analogues thereof or a mixture of universal and non-hydrogen bonding natural bases or analogues thereof. Another embodiment concerns a method of increasing the specificity of an oligonucleotide by substituting at least 5, 6, 7 or more juxtaposed nucleic acids with universal or non-hydrogen bonding natural bases or analogues thereof or a mixture of universal and non-hydrogen bonding natural bases or analogues thereof.

One embodiment is to use molecular switch-containing probes in combination with double labeled probe systems. In a further embodiment a "bridging domain" is substituted between a first and second label such that a "molecular switch" portion of the oligonucleotide contains either the first or second label. A still further aspect of this embodiment is a change in the orientation or proximity of the first and second labels to each other, such that upon said change there is a detectable change in the properties of either the first or second label or both such that correlations can be made with the "molecular switch" being "open" compared to being "closed". This embodiment then permits a direct determination of the sequence context of the portion of the target sequence that is complementary to the switch domain. In one embodiment the switch domain is designed to sense the presence or absence of a mismatch. In a still further embodiment the oligonucleotide described herein is designed such that when a mismatch is present, a quencher associated with the "switch domain becomes more closely associated with a second fluorescent label. This association selectively quenches the fluorescence of the fluorescent label when the mismatch is present. Thus, a quenched fluorescence signals the presence of a mismatch.

Molecular energy transfer (MET) is a process by which energy is passed non-radiatively between a donor molecule and an acceptor molecule. Fluorescent resonance energy transfer (FRET) is a fluorescent form of MET. FRET arises from the properties of certain chemical compounds; when excited by exposure to particular wavelengths of light, they emit light (i.e., they fluoresce) at a different wavelength. Such compounds are termed fluorophores. In FRET, energy is passed non-radiatively over a long distance (10-100 Å) between a donor molecule, which is a fluorophore, and an acceptor molecule. The donor absorbs a photon and transfers this energy non-radiatively to the acceptor. See Forster, *Z. Naturforsch.* A4:321-327 (1949); Clegg, *Meth. Enzymol.* 211:353-388 (1992).

Suitable fluorescent moieties include the following fluorophores known in the art:
4-acetamido-4'-isothiocyanatostilbene-2,2'disulfonic acid
acridine and derivatives:
  acridine
  acridine isothiocyanate
Alexa Fluor® 350, Alexa Fluor® 488, Alexa Fluor® 546, Alexa Fluor® 555, Alexa Fluor® 568, Alexa Fluor® 594, Alexa Fluor® 647 (Molecular Probes)
5-(2'-aminoethyl)aminonaphthalene-1-sulfonic acid (EDANS)
4-amino-N-[3-vinylsulfonyl)phenyl]naphthalimide-3,5 disulfonate (Lucifer Yellow VS)
N-(4-anilino-1-naphthyl)maleimide
anthranilamide
Black Hole Quencher™ (BHQ™) dyes (biosearch Technologies)
BODIPY® R-6G, BOPIPY® 530/550, BODIPY® FL
Brilliant Yellow
coumarin and derivatives:
  coumarin
  7-amino-4-methylcoumarin (AMC, Coumarin 120)
  7-amino-4-trifluoromethylcouluarin (Coumarin 151)
Cy2®, Cy3®, Cy3.5®, Cy5®, Cy5.5®
cyanosine
4',6-diaminidino-2-phenylindole (DAPI)
5',5''-dibromopyrogallol-sulfonephthalein (Bromopyrogallol Red)
7-diethylamino-3-(4'-isothiocyanatophenyl)$_4$-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansyl chloride)
4-(4'-dimethylaminophenylazo)benzoic acid (DABCYL)
4-dimethylaminophenylazophenyl-4'-isothiocyanate (DABITC)
Eclipse™ (Epoch Biosciences Inc.)
eosin and derivatives:
  eosin
  eosin isothiocyanate
erythrosin and derivatives:
  erythrosin B
  erythrosin isothiocyanate
ethidium
fluorescein and derivatives:
  5-carboxyfluorescein (FAM)
  5-(4,6-dichlorotriazin-2-yl)aminofluorescein (DTAF)
  2',7'-dimethoxy-4'5'-dichloro-6-carboxyfluorescein (JOE)
  fluorescein
  fluorescein isothiocyanate (FITC)
  hexachloro-6-carboxyfluorescein (HEX)
  QFITC (XRITC)
  tetrachlorofluorescein (TET)
fluorescamine
IR144
IR1446
Malachite Green isothiocyanate
4-methylumbelliferone
ortho cresolphthalein
nitrotyrosine
pararosaniline
Phenol Red
B-phycoerythrin, R-phycoerythrin
o-phthaldialdehyde
Oregon Green®
propidium iodide
pyrene and derivatives:
  pyrene
  pyrene butyrate
  succinimidyl 1-pyrene butyrate
QSY® 7, QSY® 9, QSY® 21, QSY® 35 (Molecular Probes)
Reactive Red 4 (Cibacron® Brilliant Red 3B-A)
rhodamine and derivatives:
  6-carboxy-X-rhodamine (ROX)
  6-carboxyrhodamine (R6G)
  lissamine rhodamine B sulfonyl chloride
  rhodamine (Rhod)
  rhodamine B
  rhodamine 123
  rhodamine green
  rhodamine X isothiocyanate
  sulforhodamine B
  sulforhodamine 101
  sulfonyl chloride derivative of sulforhodamine 101 (Texas Red)
N,N,N',N'-tetramethyl-6-carboxyrhodamine (TAMRA)
tetramethyl rhodamine
tetramethyl rhodamine isothiocyanate (TRITC)
riboflavin
rosolic acid
terbium chelate derivatives Embodiments of the oligonucleotides can contain 5' nuclease resistant regions or be modified to be resistant to 5' nuclease activity.

Embodiments also include methods of making the oligonucleotides described above. For example, one embodiment concerns a method of designing an oligonucleotide comprising a "molecular switch". In one embodiment, the method involves identifying a sequence that corresponds to or complements a target sequence and substituting 2-11 bases within said sequence with universal or non-hydrogen bonding natural bases or analogues thereof or a mixture of universal and non-hydrogen bonding natural bases or analogues thereof. It is envisioned that the substitution of the 2-11 bases creates a "bridging domain" between the target sequence and a downstream or upstream sequence in the target area. In a further embodiment, the "binding domain" has a lower affinity for its target than the sequence on the other side of the bridging domain.

For example, if a specific SNP is to be identified, the probe can be constructed to contain at least the following three domains: A first hybridizing complementary domain upstream of the SNP, a bridging domain having 2-11 substitutions as set out above, and a binding domain which recognizes the SNP. The binding domain can be constructed to have a lower affinity with the target compared to the complementary region domain. In this way, if the target does not contain the SNP, complementary may still hybridize and the binding domain will not hybridize. With the correct detection system this can be used to identify the presence of a SNP in a sample.

In one embodiment, the "bridging domain" comprises from about 2-50 universal or non-hydrogen bonding natural bases or analogues thereof or a mixture of universal and non-hydrogen bonding natural bases or analogues thereof. In a further embodiment, the "bridging domain" comprises from about 2-20, including but not limited to 3, 4, 5, 6, 7, 8, 9, 10, 11, 12, 13, 14, 15, 16, 17, 18, and 19 universal or non-hydrogen bonding natural bases or analogues thereof or a mixture of universal and non-hydrogen bonding natural bases or analogues thereof, preferably 2-12, preferably 4-12, 5-10, 4-6, 6-8, and 4-7. Alternatively 5-12 substitutions, but including 6-12, 7-12, 8-12 and 9-12. However, in some embodiments, some of these bases may be included in the hybridizable portions of the probe. In a further embodiment, the hybridizable portions of the probe may be from about 5-200 bases long, including but not limited to, 5-50, 5-20, 5-8, 5-9, 5-10, 5-11, 5-12, 5-13, 5-14, 5-15, 5-16, 5-17, 5-18, 5-19, 6-9, 7-10, and 8-12, and may include alternative bases including but not limited to: natural bases, natural base analogs, unnatural base analogs that hydrogen bond to natural bases in the target nucleic acid or other modifications. By "non-naturally occurring base" is meant a base other than A, C, G, T and U, and includes degenerate and universal bases as well as moieties capable of binding specifically to a natural base or to a non-naturally occurring base. In a further embodiment, the complementary region is comprised of more bases than the binding domain. In a further embodiment the complementary region has a higher affinity to its target than the binding domain. Thus, the binding domain which recognizes the specific sequence of interest (for example, a SNP or polymorphism) has a lower affinity than the complementary region.

A further embodiment concerns a method of substituting at least 10%, 11%, 12%, 13%, 14%, 15%, 16%, 17%, 18%, 19%, 20%, 21%, 22%, 23%, 24%, 25% or 30% of the total number of bases with universal or generic bases between complementary regions and the binding domain of the oligonucleotide. A further embodiment concerns a method of substituting at least 5%, 10%, 15%, 20%, 25%, 30%, or 40% of the total number of bases with universal or non-hydrogen bonding natural bases or analogues thereof or a mixture of universal and non-hydrogen bonding natural bases or analogues thereof between the complementary region and the binding domain.

The oligonucleotides described herein, though clearly useful for the identification of single nucleotide polymorphisms (SNPs), are also useful for other conventional methods that employ oligonucleotides (e.g., diagnostics, hybridization, sequencing, etc). The oligonucleotides described herein can be used in most methods known to one of skill in the art in which conventional oligonucleotides are used. Although many methods concern the use of said oligonucleotides to detect SNPs, further embodiments also encompass the use of said oligonucleotides as primers (e.g., in conjunction with the TAQMAN™ assay, PCR, or RT-PCR), as probes (e.g., in conjunction with the HPSA™, MOLECULAR BEACON™, HYBPROBE™, CPT™ and INVADER™ assays, northern, Southern, or library hybridizations), in arrays (e.g., chip-based arrays, peptide/nucleic acid virtual arrays, DNA microarrays, antisense scanning arrays, or plate-type arrays) and in other techniques involving oligonucleotides (e.g., 5' or 3' RACE or related techniques). The term "probe" is used herein to mean an oligonucleotide to detect a target nucleic acid or to immobilize a target sequence, whereas, the term "primer" is used to refer to an oligonucleotide, which can be used to amplify or extend a target nucleic acid. Thus, several embodiments concern diagnostic methods that employ the embodied oligonucleotides in conjunction with a conventional diagnostic technique.

The oligonucleotides can be of virtually any sequence and of any length, wherein said oligonucleotides comprise at least 5%, 6%, 7%, 8%, 9%, 10%, 11%, 12%, 13%, 14%, 15% or more or up to and including 50% universal or non-hydrogen bonding natural bases or analogues thereof or a mixture of universal and non-hydrogen bonding natural bases or analogues thereof, wherein at least 5% of the bases separate the complementary region and the binding domain. Further, wherein the binding domain recognizes a specific sequence, such as a SNP or polymorphism. The term "oligonucleotide" is used to refer to a molecule consisting of DNA, RNA, or DNA/RNA hybrids with or without non-nucleic acid analogues and polymers. In some embodiments the universal non-hydrogen bonding natural bases or analogues thereof or a mixture of universal and non-hydrogen bonding natural bases or analogues thereof are juxtaposed and, in others, clusters of at least two universal non-hydrogen bonding natural bases or analogues thereof or a mixture of universal and non-hydrogen bonding natural bases or analogues thereof are present in the oligonucleotide sequence. In one embodiment, sequences correspond to already existing probes, which can be used to identify the presence or absence of a SNP or other genetic marker that has an association with a disease. Exemplary sequences are those that indicate a predilection to contract cystic fibrosis (See e.g., U.S. Pat. No. 6,201,107, hereby expressly incorporated by reference in its entirety), sickle cell anemia (See e.g., U.S. Pat. No. 4,683,194, hereby expressly incorporated by reference in its entirety), hemochromatosis (See e.g., U.S. Pat. No. 6,025,130, hereby expressly incorporated by reference in its entirety), and cancer (See e.g., U.S. Pat. No. 6,194,158, hereby expressly incorporated by reference in its entirety). It should be understood that other sequences known by those of skill in the art, which indicate a predilection to disease can be used to generate the oligonucleotides described herein.

Oligonucleotide synthesis is well known in the art, as is the synthesis of oligonucleotides containing modified bases and backbone linkages. In fact, such oligonucleotides can often be obtained from commercial suppliers upon providing the supplier with the specific sequence and composition information and a request for custom production. Although in most cases, the length of the oligonucleotides is less than 100 bases, embodiments can be from about 5 to about 10,000 nucleotides in length, more particularly, 10 to about 300 nucleotides in length, preferably 12 to about 200 nucleotides in length, preferably, 15 to about 100 nucleotides, more preferably 17 to about 50 nucleotides, and most preferably, about 20 to about 40 nucleotides in length.

The oligonucleotides can employ any backbone and any sequence capable of resulting in a molecule that hybridizes to target DNA and/or RNA. Examples of suitable backbones include, but are not limited to, phosphodiesters and deoxyphosphodiesters, phosphorothioates and deoxyphosphorothioates, 2'-O-substituted phosphodiesters and deoxy analogs, 2'-O-substituted phosphorothioates and deoxy analogs, morpholino, PNA (U.S. Pat. No. 5,539,082, hereby expressly incorporated by reference in its entirety), 2'-O-alkyl methylphosphonates, 3'-amidates, MMI, alkyl ethers (U.S. Pat. No. 5,223,618, hereby expressly incorporated by reference in its entirety) and others as described in U.S. Pat. Nos. 5,378,825, 5,489,677 and 5,541,307, all of which are hereby expressly incorporated by reference in its entirety. Where RNase activity is desired, a backbone capable of serving as an RNase substrate is employed for at least a portion of the oligonucleotide.

Universal non-hydrogen bonding natural bases or analogues thereof or a mixture of universal and non-hydrogen bonding natural bases or analogues thereof suitable for use with the embodiments described herein include, but are not limited to, 5-nitroindole deoxyriboside, 3-nitropyrrole deoxyriboside, 4-nitrobenzimidazole deoxyriboside, deoxy nebularine, deoxyinosine, 2'-OMe inosine, 2'-OMe 5-nitroindole riboside, 2'-OMe 3-nitropyrrole riboside, 2'-F inosine riboside, 2'-F nebularine, 2'-F 5-nitroindole riboside, 2'-F 4-nitrobenzimidazole riboside, 2'-F 3-nitropyrrole riboside, PNA-5-introindole, PNA-nebularine, PNA-inosine, PNA-4-nitrobenzimidazole, PNA-3-nitropyrrole, morpholino-5-nitroindole, morpholino-nebularine, morpholino-inosine, morpholino-4-nitrobenzimidazole, morpholino-3-nitropyrrole, phosphoranidate-5-nitroindole, phosphoramidate-nebularine, phosphoramidate-inosine, phosphoramidate-4-nitrobenzimidazole, phosphoramidate-3-nitropyrrole, 2'-O-methoxyethyl inosine, 2-'O-methoxyethyl nebularine, 2'-O-methoxyethyl 5-nitroindole riboside, 2'-O-methoxyethyl 4-nitro-benzimidazole riboside, 2'-O-methoxyethyl 3-nitropyrrole riboside, deoxy $R_p$MP-5-nitroindole dimer 2'-Ome $R_p$MP-5-nitroindole dimer as well as the natural bases A, T, C, G and U and analogs thereof.

In one embodiment, the oligonucleotides are characterized in that they share the formula: "XRY", wherein "X" consists of about 5-10, 11-20, or 5-20 natural or/modified nucleic acid bases; "R" consists of about 2-5, 6-10, or 2-10 juxtaposed universal non-hydrogen bonding natural bases or analogues thereof or a mixture of universal and non-hydrogen bonding natural bases or analogues thereof (corresponding to the bridging domain); and "Y" consists of about 2-5,6-10, 11-15, or 3-20 nucleic acid bases; wherein X, R, and Y are covalently joined and at least 1%, 2%, 3%, 4%, 5%, 6%, 7%, 8%, 9%, 10%, 11%, 12%, 13%, 14%, or 15% or up to and including 50% of the total number of bases are universal or non-hydrogen bonding natural bases or analogues thereof or a mixture of universal and non-hydrogen bonding natural bases or analogues thereof and X and/or Y might contain a natural or unnatural base at the SNP sight (or polymorphism) and X and/or Y might contain higher or lower affinity bases or analogues. In a further embodiment, Y contains the polymorphism and X has a higher affinity for its target than Y. In a further embodiment, the polymorphism may also be a variant region in a virus or other infectious agent, a variant region in a microbe, plant or animal, or a mutation.

The oligonucleotides described herein can be sold separately or can be incorporated in kits that facilitate genetic analysis. For example, many diagnostic kits are currently available to detect unique nucleic acid sequences, expression levels of particular genes, and SNPs. These kits typically provide oligonucleotide primers and/or probes, which are to be used to detect a specific target sequence associated with a disease or conditions, or to detect the presence of infectious organisms. Embodiments include diagnostic kits comprising probes and primers that are manufactured in accordance with the oligonucleotide structures described herein. That is, embodiments include diagnostic kits comprising at least one oligonucleotide comprising a "molecular switch" as disclosed herein. The kits may optionally provide a support (e.g., nitrocellulose, nylon, plastic, or other macromolecule), hybridization or amplification reagents, and instructions. The section below describes in greater detail many of the methods concerning the oligonucleotides described herein.

Methods

The oligonucleotides described herein have many utilities including the detection of SNPs and including, but not limited to, application in other diagnostic processes, expression analysis, array technology, sequencing, hybridization and other techniques, which use conventional oligonucleotides. The oligonucleotides described herein can be used in most methods known to one of skill in the art in which conventional oligonucleotides are used.

By one approach, a method of detecting the presence or absence of a mutation or polymorphism in a sample comprising nucleic acids is practiced by contacting said nucleic acid with at least one of the oligonucleotides described above, and identifying whether the switch domain of the probe is in the "open" or "closed" position, in response to the sequence context of the target molecule. In a further embodiment, the universal or non-hydrogen bonding natural bases or analogues thereof or a mixture of universal and non-hydrogen bonding natural bases or analogues thereof of said oligonucleotides are not located at the site or sites of mutation or polymorphism but unnatural bases allowing higher SNP discrimination might be. Additionally, this method can incorporate an amplifying step (e.g., PCR or RT-PCR, or T7 or SP6 or rolling circle mediated amplification) to aid in the identification of the presence or absence of the mutation or polymorphism. The section below describes the oligonucleotides comprising "molecular switches" in greater detail. Embodiments also include methods of making and using the oligonucleotides described above. One embodiment concerns a method of designing an oligonucleotide, which involves identifying a sequence that corresponds to or complements a target sequence and designing an oligonucleotide comprising a molecular switch which is specific to the target sequence. By one approach, a sequence that interacts with a target that indicates the presence or absence of a disease is selected from U.S. Pat. Nos. 6,201,107; 4,683,194; 6,025,130; or 6,194,158 (all of which are hereby expressly incorporated by reference in their entireties). Care should be taken such that the diagnostic site (e.g., site of the SNP or mutation) is not covered by the universal bases, but may be covered by an unnatural base to enhance SNP discrimination.

Thus, the oligonucleotides described herein are useful for the identification of any mutations, allelic variants, polymorphisms, and the normal or wild-type sequence of a gene. In addition, the oligonucleotides described herein may be used to detect the presence of a sequence, or alternatively, the oligonucleotides may be used to identify the amount of a particular mRNA which is being produced by a cell. The quantitation may be in addition to, or separately from the identification of the presence of a specific target sequence.

However, because the most common type of human genetic variation is the single-nucleotide polymorphism (SNP), a base position at which two alternative bases occur at appreciable frequency (>1%) in the population, the utilization of SNPs for clinical diagnostics, whole-genome linkage disequilibrium screens, determination of the recent evolutionary history of a species, and the process of speciation has become a major focus of human genetics. Thus, methods of genotyping or determining the presence or absence of a mutation or polymorphism, for example a SNP, using the oligonucleotides described herein are extremely useful embodiments.

A prototypical example of the forthcoming primary public health role of molecular diagnostics (particularly of SNPs) is the identification of individuals affected by or at-risk for the iron overload disorder hereditary hemochromatosis. More than 90% of the cases of this most common of all single-gene disorders (present in 0.5% of whites) are caused by the presence of a homozygous well-conserved single nucleotide substitution (nucleotide G845A; amino acid C282Y) in the transferrin receptor binding protein HFE. This loss-of-function mutation abolishes HFE's usual cell surface expression, thus preventing its ability to down-regulate the affinity of transferrin receptor for transferrin-bound iron and resulting in a constitutive iron adsorption.

Accordingly, an individual at risk for hemochromatosis can be identified by selecting probes or primers that allow for the detection of the well-conserved single nucleotide substitution, nucleotide G845A. (See e.g., U.S. Pat. No. 6,025,130, hereby expressly incorporated by reference in its entirety, wherein specific primers and probes can be obtained). Once suitable probes are selected they can be designed to contain a "molecular switch" as taught herein and used to identify whether said individual has the mutation that indicates the disease.

In a similar fashion, an individual at risk for cystic fibrosis (CF) can be identified (suitable primers or probes are identified in U.S. Pat. No. 6,201,107), an individual at risk of contracting cancer can be identified (suitable primers and probes are identified in U.S. Pat. No. 6,194,158, hereby expressly incorporated by reference in its entirety), and an individual at risk for sickle cell anemia can be identified (suitable primers and probes are identified in U.S. Pat. No. 4,683,194, hereby expressly incorporated by reference in its entirety).

In a particular embodiment, the molecular switch may be used to obtain SNP and/or expression information using arrays or solid surfaces. Probes containing a molecular switch are first hybridized with potential target nucleic acids that may be arranged on a solid surface, for example, in an array format as is known in the art. Following hybridization, the probes are digested (for a SNP assay) or extended to incorporate a detectable label (for an expression assay). If the switch is "open" it will be digested (for a SNP assay) or not extended (for an expression assay); if the switch is "closed" it is protected from digestion and the probe label is preserved (for a SNP assay) or extended to incorporate a detectable label (for an expression assay). The switch probes may then be sorted according to unique sequence elements on each probe, or specific binding partners on each probe. In a SNP assay, if the label in the switch portion is still present, the switch was closed during hybridization; if the label in the switch portion is lost, the switch was open during hybridization. In an expression assay, if an incorporated label is present (due to extension during hybridization), the switch was closed; if no label is present, the switch was open and no target was present.

In another particular embodiment, biological probes may be designed containing a molecular switch. A primer may be designed containing a molecular switch, and then extended biologically to produce long probes with a switch built into their ends. This provides a method of building a complex and long probes that retain the ability to resolve mismatches due to the built in molecular switch.

The following examples describe in greater detail techniques that can be used to make the oligonucleotides described herein and show the advantages and improvements of the oligonucleotides containing "molecular switches". The "molecular switch" produced improved specificity over a very wide temperature range and can be interfaced directly into amplification assays, including PCR assays, assays using T7 and SP6 amplification, rolling circle amplification assays, nuclease protection assays, and expression assays.

The invention will now be described in greater detail by reference to the following non-limiting examples.

EXAMPLES

The Hemochromatosis gene was used as a prototype polymorphism in the following examples. The performance of double labeled probes which targeted the Hemochromatosis gene target H63D were evaluated as to melting temperature, and in standard PCR assays. The H63D position of the hemochromatosis gene has a G residue at position 418 which is transmutated to a C in one of the genetic alterations that is responsible for hemochromatosis. Exemplary probes and targets are shown in Table 1 below.

Example 1

Ultraviolet melting curve measurements were carried out to determine if the switch domain of the probe could be controlled to be "open" or "closed" by the influence of a single mismatch.

Melting temperatures were determined for probes containing universal bases under standard PCR buffer conditions and the results were compared to those obtained using a control sequences without the universal bases (Mu/Mu and Wt/Wt). See Table 1 for Probe and oligonucleotide target sequences. The sequences for these studies were provided by TriLink BioTechnologies, and prepared using conventional phosphoramidite DNA synthesis chemistry. The melting curve measurements were done using UV Optical Melts with Wild type (Wt) and Mutant (Mu) single strand targets in PCR reaction buffer minus dNTPs. The probes included X1WtH63D (SEQ ID NO:1), X2 WtH63D (SEQ ID NO:2), X3 WtH63D (SEQ ID NO:3), X4 WtH63D (SEQ ID NO:4), X5 WtH63D (SEQ ID NO:5), X7 WtH63D (SEQ ID NO:7), X8 WtH63D (SEQ ID NO:8), X9 WtH63D (SEQ ID NO:9), X10 WtH63D (SEQ ID NO:10), X11 WtH63D (SEQ ID NO:11), X14 HFE63DWt (SEQ ID NO:14), and X15 HFE63DMu (SEQ ID NO:15). The targets were matched or mismatched single strand targets (Mu and Wt) with short overlaps to the probes and included AntH63DWt (SEQ ID NO:13), AntH63DMu (SEQ ID NO:18), AntH63DWtLong (SEQ ID NO:19), and AntH63DMuLong (SEQ ID NO:20). Target controls were also included in the sense instead of antisense orientation and included SenH63DWt (SEQ ID NO:12) and SenH63DMu (SEQ ID NO:17). The concentration of oligonucleotide probes and targets were at 0.35 to 0.40 O.D. each per milliliter in a buffer system designed for PCR reactions:

TABLE 1

Hemochromatosis probes and targets

| Probe/target | type | SEQ ID NO: | Sequence |
|---|---|---|---|
| X1WtH63D | Mod. | 1 | 5'PS-U-G-A-FAM-ccagctgttcgtgtBBBBBgatcatg-BHQ1 |
| X2WtH63D | Mod. | 2 | 5'PS-t-g-a-FAM-ccagctgttcgtgtBBBBBgatcatg-BHQ1 |
| X3WtH63D | Mod. | 3 | 5'PS-U-G-A-ccagctgttcgtg-FAM-ttcBBBBatcatgag-BHQ1 |
| X4WtH63D | Mod. | 4 | 5'PS-t-g-a-FAM-ccagctgttcgtgtBBBBBgatcat-BHQ1 |
| X5WtH63D | Mod. | 5 | 5'PS-t-g-a-FAM-ccagctgttcgtgtBBBBBBatcat-BHQ1 |
| X6WtH63D | Mod. | 6 | 5'PS-t-g-a-ccagctgttcg-FAM-tgtBBBBBBatcat-BHQ1 |

TABLE 1-continued

Hemochromatosis probes and targets

| Probe/target | type | SEQ ID NO: | Sequence |
|---|---|---|---|
| X7WtH63D | Mod. | 7 | 5'PS-t-g-a-FAM-ccagctgttcgtgtS18S18S18atcat-BHQ1 |
| X8WtH63D | Mod. | 8 | 5'-PS-c-c-a-FAM-gctgttcgtgtBBBBBgatcat-BHQ1 |
| X9WtH63D | Mod. | 9 | 5'APS-t-g-a-ccagctgttcg-FAM-tgtBBBBBgatcatg-BHQ1 |
| X10WtH63D | Mod. | 10 | 5'APS-t-g-a-ccagctgttc-FAM-gtgtBBBBBgatcat-BHQ1 |
| X11WtH63D | Mod. | 11 | 5'APS-t-g-a-ccagctgttcg-FAM-tgtBBBBtgatcatgag-BHQ1 |
| SenH63DWt | DNA | 12 | 5'-tggatgaccagctgttcgtgttctatgatcatgagagt |
| AntH63DWt | DNA | 13 | 5'-actctcatgatcatagaacacgaacagctggtcatcca |
| X14HFE63D Wt | Mod. | 14 | 5'APS-g-a-t-ccagctgttcgt-FAM-BBBBtatgatcatgaga-BHQ1 |
| X15HFE63D Mu | Mod. | 15 | 5'APS-g-a-t-ccagctgttcgt-FAM-BBBBtatgatgatgaga-BHQ1 |
| X16HFE63D WtTand | DNA | 16 | 5'-gatgatgBBBBBtcgccgtgtggagccccgaa |
| SenH63DMu | DNA | 17 | 5'-tggatgaccagctgttcgtgttctatgatgatgagagt |
| AntH63DMu | DNA | 18 | 5'-actctcatcatcatagaacacgaacagctggtcatcca |
| AntH63DWt Long | DNA | 19 | 5'-cacggcgactctcatgatcatagaacacgaacagctggtcatccacgta |
| AntH63DMu Long | DNA | 20 | 5'-cacggcgactctcatcatcatagaacacgaacagctggtcatccacgta |
| HFEr91Wt | DNA | 21 | 5'-agccacatctggcttgaaattctactggaaacccatggagttcggggctccacacggcgactctcatgatcatagaacacgaacagctggtca |
| HFEr91Mu | DNA | 22 | 5'-agccacatctggcttgaaattctactggaaacccatggagttcggggctccacacggcgactctcatcatcatagaacacgaacagctggtca |

PS=phosphothioates; APS=propylthiophosphate; the bolded and underlined "U-G-A" corresponds to 2'ribonucleotides (RNA); the bolded and underlined "t-g-a" or "c-c-a" corresponds to deoxy nucleotides (DNA); FAM is a 6-carboxy-N-hydroxysuccinide-fluorescein label that was conjugated to an C7 Unilinker (Clontech) which was inserted into the sequence during DNA synthesis. The BHQ1 is a black hole quencher; the S18 is a spacer. SEQ ID NOs:12, 13, and 16-22 are target sequences either sense (sen) or antisense (ant). SEQ ID NOs:1-11, 14 and 15 are all probes with various modifications.

TABLE 2

Reaction Buffer 50 mM KCL
10 mM Tris-HCl, pH 7.5
2.5% Sucrose
2.5 mM MgCl2

Multiple melting temperature determinations were performed for each probe/target combination. All mixtures were heated to 85-95° C. for 10-15 minutes and allowed to cool to room temperature before use. Melting temperatures were determined by UV absorbance in sealed quartz cuvettes using a Varian Cary 3E UV-Visible Spectrophotometer with a Varian Cary temperature controller, controlled with Cary 01.01(4) Thermal software. Temperature gradients decreased from 90° C. to 20° C. at 1° C. per minute.

Figure 3:
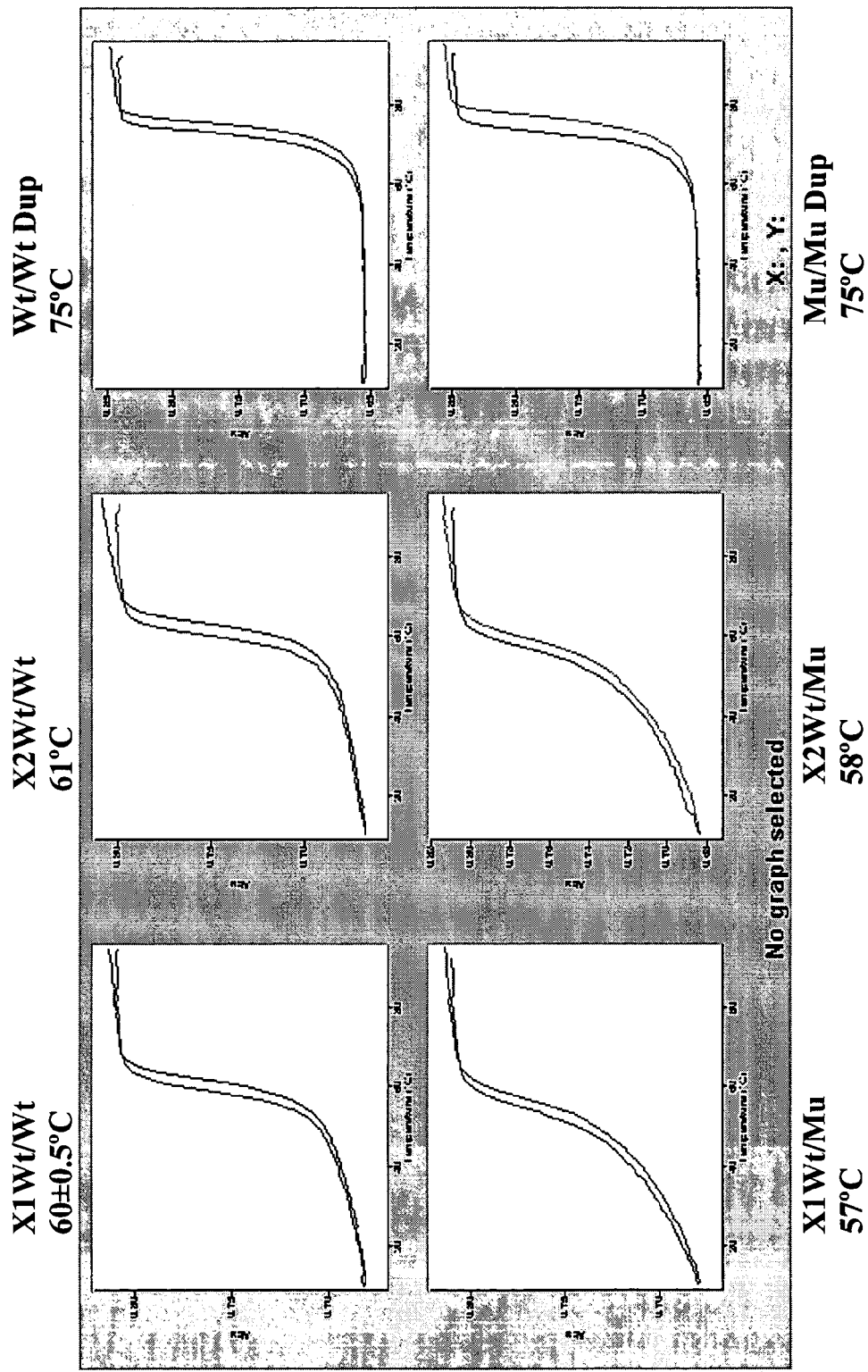
FIG. 3 depicts the results of melting curves (as measured by absorbance) using various Specimer™ Hemochromatosis probes containing molecular switches, detecting both wild type (Wt) and mutant (Mu) target sequences in PCR reaction buffer minus dNTPS. As can be seen, a mismatch produces a biphasic profile indicative of the molecular switch melting at a much lower $T_m$ than the rest of the probe.

As shown in FIG. 3, probes containing a molecular switch show multi-phasic melting, demonstrating that the molecular switch melts at a much lower temperature than the rest of the probe, but only when a mismatch is present.

As a control for melts representative of duplexes containing all natural bases the SenH63DWt was hybridized and melted with the AntH63DWt and likewise melts between SenH63DMu and AntH63DMu were carried out. The results showed classic sigmoid melts profiles with $T_m$s centered around 75° C. in both cases. The cross hybridization of the SenH63DWt sequence with the AntH63DMu, as well as the SenH63DMu with the AntH63DWt showed identical sigmoid melt profiles with the exception that the $T_m$s were reduced to 71-72° C. The small reduction in $T_m$ of approximately 3-4° C. was a result of the presence of a mismatch in the mismatched duplexes.

In a similar manner probes X1-X10 were all hybridized to the AntH63DWt and AntH63DMu sequences. When hybridized with AntH63DWt all the probes showed a classic sigmoid melting profile similar to those seen for the control sequences with $T_m$s ranging from about 50 to 62° C. When sequence X1-X10 were hybridized with the AntH63DMu target the melting profiles became biphasic with two transition becoming apparent. At higher temperatures in the 50 to 60° C. range a sigmoid profile remained, but in addition there was a second transition that appeared as a shoulder and extended all the way down to 20° C. One notable exception to this trend, was the X7 probe that showed a weak shoulder in comparison to the other probes.

These results are direct evidence that in the presence of mismatches the "molecular switch" portion of the probe opens in response to a mismatch under conditions that the remainder of the probe remains largely hybridized. In addition to demonstrating a shoulder in the UV melts, many of these probes also showed a decrease in $T_m$ for the entire probe due to the opening of the switch portion in response to a mismatch. Examples of probes that showed a drop in overall $T_m$ upon opening of the switch include, X1, X2, X3, X4, X8, X9 and X10. Probes that showed little drop in $T_m$ when the switch opened in response to a mismatch were X5 and X6. Thus depending on the structure and properties of the switch it may or may not have an effect on overall $T_m$ of a probe in response to a mismatch. FIG. 3 shows typical UV melt profiles and illustrates the results for the X1WtH63D and X2WtH63D probes with their corresponding match (AntH63DWt) and mismatch targets (AntH63DMu) target sequences.

Example 2

The annealing and melting of the probes described in EXAMPLE 1 were retested but measured by fluorescence rather than UV. The presence of a perfect match was compared to mismatched single stranded targets.

The assay was performed as follows: oligonucleotide probes and separately targets were diluted to a concentration of 400 µM into water: 16 µL into 384 µL of water, making a 16 µM working stock. Then, 12.0 µL of each nucleic acid dilution(s) and/or water was added up to 25 µL total into 25 µL of 2× LIFETECH SUPERSCRIPT PCR reaction buffer to make 50 µL total final volume. The assay measured the FAM/BHQ1 interaction directly. The final probe concentration was 4 µM.

Reactions were performed in an MJ RESEARCH DNA Engine Opticon Fluorescence Detection System (MJ Research, Waltham, Mass.). After an incubation of 2-5 min. at 95° C. and cooling to 20° C. for 2-15 minutes, the mixtures were ramped from 20° C. to 95° C. at a rate of 2° C. per minute. Fluorescence was measured every 0.5° C.

The probes were identical to those in Table 1. For probes X1-X10 listed in Table 1 fluorescent hybridization data were obtained for the probe alone, the probe hybridized with AntHFE63DWt, and the probe hybridized to AntHFE63DMu. In all cases, the probes showed the desired hybridization with the wildtype sequence, and this hybridization was characterized by high fluorescence at 20° C. with slight decreases in fluorescence until the temperature approached 50-60° C. at which point there was a strong decrease in fluorescence. For each of the probes the sharp drop in fluorescence corresponded to the $T_m$s that were measured in EXAMPLE 1. This verified that the probes were all hybridizing to the wild-type target at temperatures below 50-60° C. and that the fluorescence was increased due to the spacial separation of the fluorescer and the quencher upon hybridization. Upon melting at higher temperatures the fluorescer and quencher were no longer spacially separated and were free to come into closer contact with each other. Melting of the probe and target were further characterized by the fluorescence being reduced to that of the probe alone in solution.

In comparison to the melting profiles of the probes with the wildtype target AntHFE63DWt, all the probes showed a decrease in fluorescence, with the exception of X7, all the way down to 20° C. This verified as had already been demonstrated by the UV melting studies in EXAMPLE 1, that the molecular switch portion of the probes were opening in response to a mismatch and that the effect of the switch being at least partially open was observed all the way down to 20° C. Comparing the fluorescent melting profiles for the wildtype verses the mutant (mismatched) targets there were several important observations. First, upon opening of the switch portion of the probe in response to a mismatch some probes showed a reduction in the overall $T_m$ of the entire probe while others did not. Probes X1, X2, X3, X4, X8, X9 and X10 showed drops in $T_m$, while probes X5 and X6 did not. This observation correlated with the UV measurements of EXAMPLE 1 where the same observation was made. These differences correlate with the size of the binding domain of the molecular switch. Those with fewer hydrogen bonding bases in the binding domain, probes X5 and X6, do not effect the $T_m$ of the probe when the switch opens, while those with more hydrogen bonding bases, X1, X2, X3, X4, X8, X9 and X10, do effect the $T_m$. This observation further correlates with the ability of the switch portion of the probe to contribute to the overall stability of the probe when hybridized to the wild-type target. When the binding domain of the switch is longer and as a result is more stable, it contributes affinity to the probe with a wild-type target. When the binding domain is shorter and is less stable, it contributes little or no affinity for the wild-type target. As a result, with low affinity binding domains, upon opening of the switch there is no change of affinity of the probe for the target, since the binding domain of the switch was not contributing significant stability to the probe for the target when it was hybridized. What this demonstrates is that it is readily possible to design the switch portions of the probe to either have an effect on the overall $T_m$ of the probe upon opening, or alternatively to design the switch to have little or no effect upon opening. Thus the switch portion can be easily designed to provide different overall hybridization characteristics depending upon the hybridization system one wishes to develop.

A second observation was that the fluorescence associated with free probe was about five times or more higher for X1, X2, X4, X5, X7, and X8 than it was for X3, X6, X9 and X10. This correlated with the spacing between the fluorescer and quencher. Excluding X7, free probes with higher free probe fluorescence showed spacing between the fluorescer and quencher of 22-26 nucleotides, while probes with lower fluorescence had a spacing of 14-15 nucleotides. In many hybridization formats lower signals from free probe are desirable, and this observation indicates that free probe signal can be controlled by adjusting the spacing between the labels in use (in this case a quencher and fluorescer).

A third observation was that the X7 probe, that contained an unstructured flexible S18 spacer in the bridging domain portion of the molecular switch, worked poorly compared to the probes that contained universal bases in the bridging domain. It showed no $T_m$ discrimination between the matched and mismatched targets, it had very high fluorescence associated with free probe, and it gave poor reduction in fluorescence in response to the presence of the mismatched target.

Figure 4:
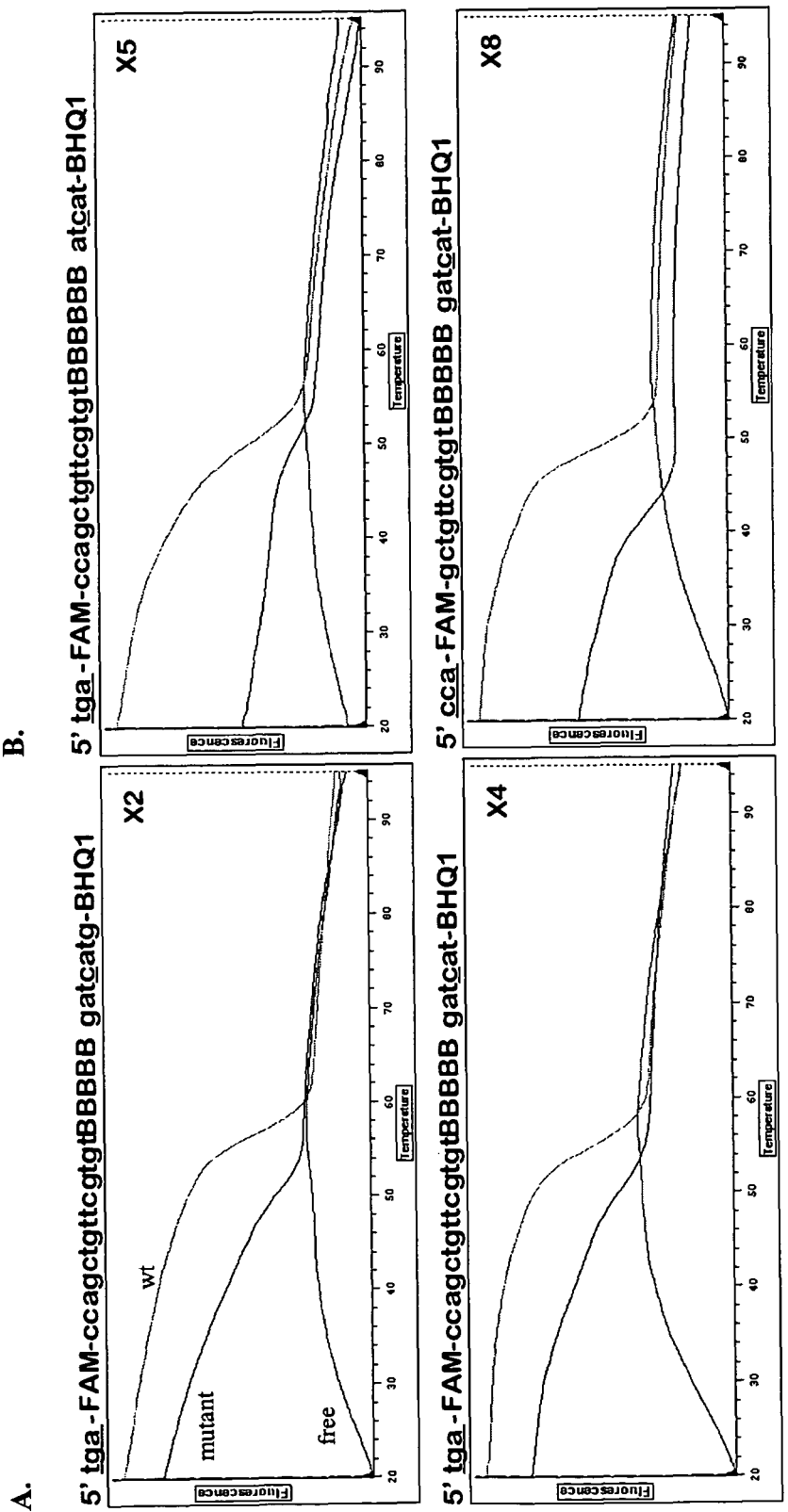
FIG. 4 collectively depicts the results of melting curves (as measured by fluorescence) using various Specimer™ Hemochromatosis probes containing molecular switches with terminal FAM constructions.
Figure 5:
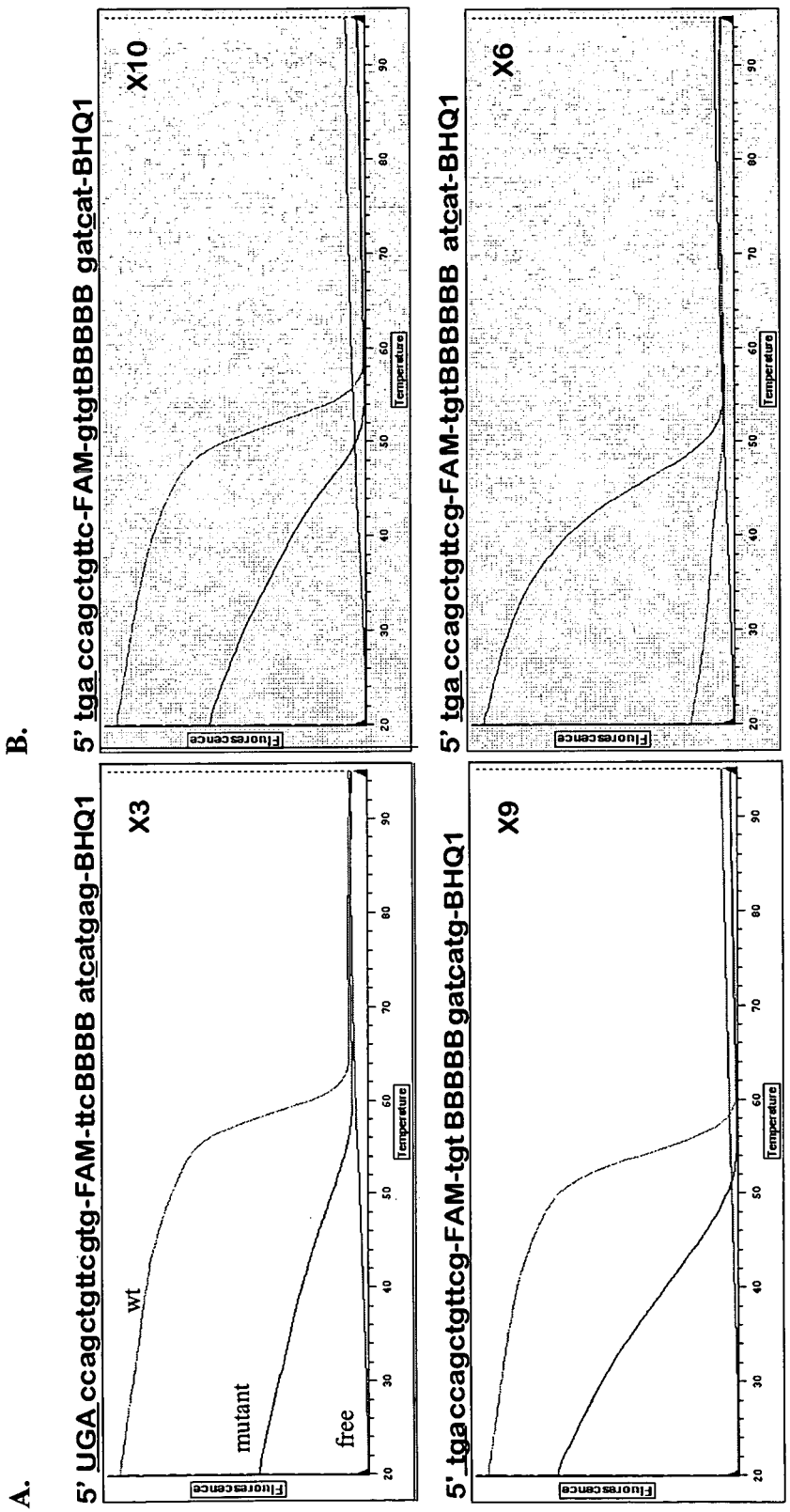
FIG. 5 collectively depicts the results of melting curves (as measured by fluorescence) using various Specimer™ Hemochromatosis probes containing molecular switches with internal FAM constructions.

Overall this example demonstrates the utility of molecular switch constructions for discriminating matched and mismatched targets. In addition, it demonstrates the ability to control signal associated with free probe, as well as the ability to design the switch portion of oligonucleotides for a range of desired effects depending on the way in which the molecular switch containing oligonucleotides are used. FIG. 4 (using probes with terminal FAM constructions) and FIG. 5 (using probes with internal FAM constructions) clearly illustrate these points.

Example 3

Figure 6:
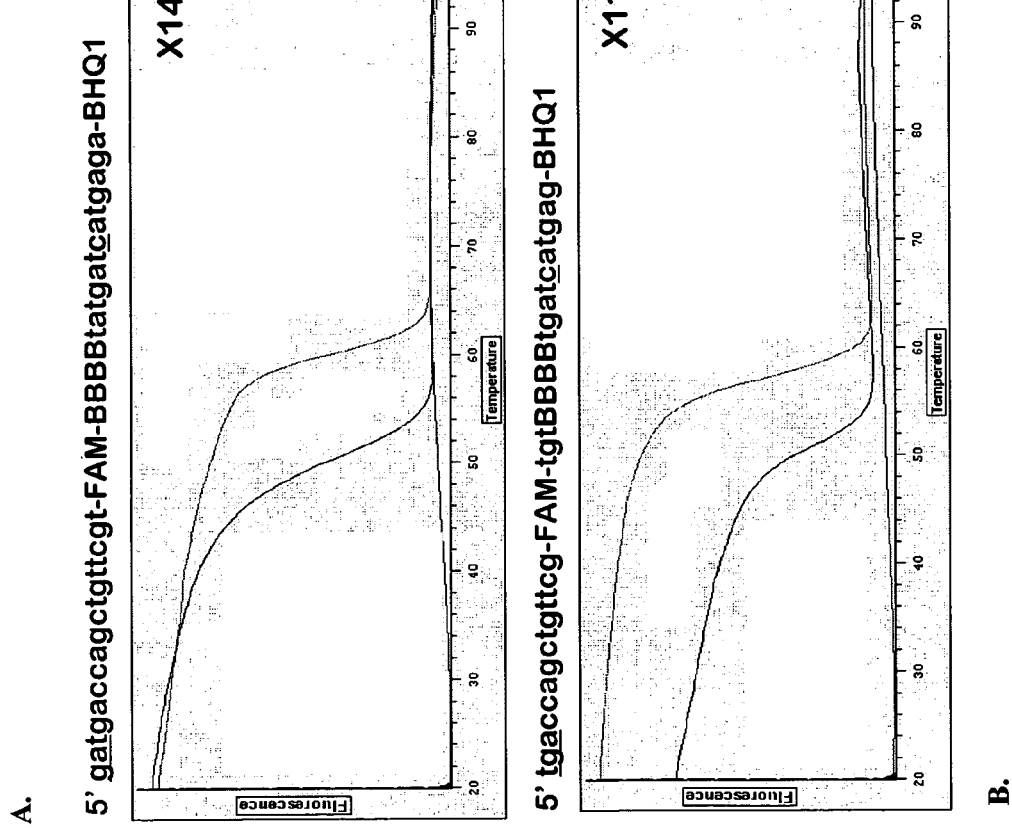
FIG. 6 collectively depicts the results of melting curves (as measured by fluorescence) using various longer Specimer™ Hemochromatosis probes containing molecular switches.

This example was run under the same conditions as EXAMPLE 2 with the exception that the probe sequences were the X11 and X14 probe sequences and the target sequences were the AntH63DWtLong (match) and AntH63DMuLong (mismatch). The purpose of this example was to examine the effect of yet longer switch sequences. This example demonstrated that further lengthening the switch portion of the probe gives greater separation in $T_m$ between match and mismatch targets, but at the same time the discrimination at much lower temperature (20° C.) was reduced or lost all together in the case of the X14 probe. Thus, the melting temperature characteristics of switch containing probe can be further attenuated to match desired use conditions by further lengthening the switch portion. FIG. 6 clearly shows the effects on melting characteristic when the switch portion of these probes is lengthened.

Example 4

The performance of double labeled probes which targeted the Hemochromatosis gene target H63D were evaluated in the following standard PCR assay. In this experiment double labeled probes containing a molecular switch were evaluated. The double labels were black hole quencher 1 (BHQ1) and the fluorescent label FAM. In addition to the double labels the 5' portions of the oligonucleotides were rendered resistant to the 5' exonuclease activity by incorporating three phosphothioate linkages at the 5' end together with a terminal 5' thiophosphate, a terminal 5'-alkylthiophosphate, or a terminal 5'thiophosphate as well as three 2'-OMe containing nucleotides.

PCR was performed by amplifying 10 ng of human placental genomic DNA in a 50 µl volume using the GENEAMP PCR CORE REAGENT KIT reagents (Applied Biosystems, Foster City, Calif.). The following conditions were used: 1% (vol/vol) glycerol, 1×PCR Buffer II, 5 mM $MgCl_2$, 200-500 µM dNTP mix, 150 nM of forward and reverse primers, 200 nM of various probes listed in Table 1, and 5 U AMPLITAQ DNA Polymerase. The primers were the same as those used by Ugozzoli et. al. (*Anal. Biochem* 0.307:47-53, 2002) and are listed in Table 3 below.

TABLE 3

| PCR Primers | Type | SEQ ID NO: | Sequence (5' to 3') |
|---|---|---|---|
| H63D-F-primer | DNA | 23 | cct ggt ctt tcc ttg ttt gaa g |
| H63D-Rev-primer | DNA | 24 | aca tct ggc ttg aaa ttc tac t |

After an incubation of 4 min. at 95° C. to activate AMPLITAQ, the following cycling protocol was run: 50 cycles of denaturation at 95° C. for 15 sec, then annealing at 50-54° C. for 45 s to 90 s, and extension at 72° C. for 60 s. Reactions were performed in an MJ Research DNA Engine Opticon Fluorescence Detection System (MJ Research, Waltham, Mass.). The fluorescent data generated by the hybridization of the probes were collected during the PCR annealing step, during extension, and at denaturation. Data analysis was performed by analyzing real-time amplification plots with the Opticon software. Melting temperatures were determined after completion of the PCR cycle. After an incubation of 2-5 min. at 95° C. and cooling to 20° C. for 2-15 minutes, the mixtures were ramped from 20° C. to 95° C. at a rate of 2° C. per minute. Fluorescence was measured every 0.5° C.

Figure 7:
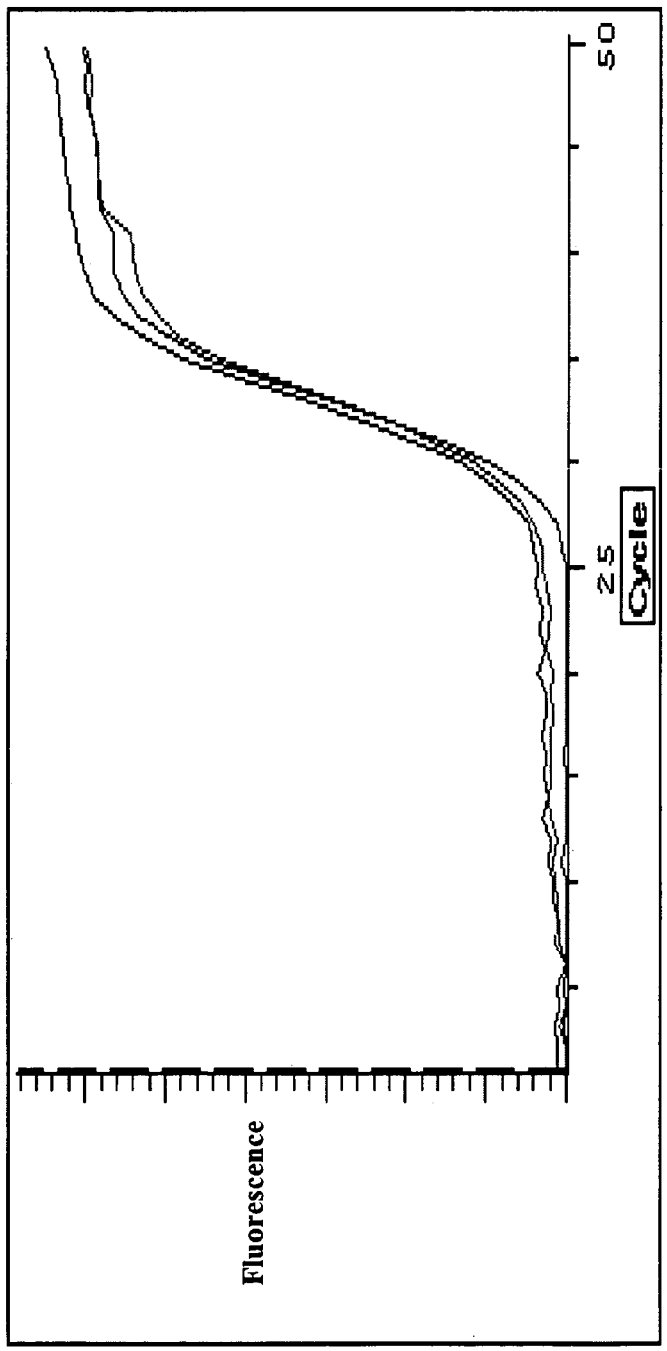
FIG. 7 depicts the results of quantitative PCR using Specimer™ Hemochromatosis probe X2WtH63D (SEQ ID NO:2) containing a molecular switch.

As a specific example the X2WtH63D (SEQ ID NO:2) probe was evaluated using 10 ng of placenta derived human genomic DNA as input. The assay was done in triplicate. Results showed a classic exponential response with a Ct (cycling time) of 26 for all three replicates. This result indicated the utility of these probes in a quantitative PCR assay format, and the reproducibility of results. FIG. 7 shows the results of this assay.

Example 5

As a test of the nuclease stability of probes, post PCR assay melts were carried out to determine if probes had been degraded during PCR amplification. A PCR reaction identical to that in Example 3 was performed and the resulting probe target interactions were analyzed as to melting temperature. The probe X3WtH63D (SEQ ID NO:3) was used against wild-type human genomic DNA.

The results showed that the probe had a melting temperature of approximately 58° C. which was the same melting temperature observed for this probe by UV melting studies in EXAMPLE 1 and the fluorescence melting measurements in EXAMPLE 2. In addition, upon melting to produce free probe, fluorescence was reduced to the level of free probe. Both of these observations indicate that the probe remains largely, in not completely intact through the entire PCR amplification process. If the probe had been degraded or partially degraded, it would be expected to show a difference in $T_m$. In addition, if the probe were degraded, the fluorescent label would have become separated from the quencher, and upon melting the quencher would have no longer had an effect on the fluorescer. This method also shows the ability to obtain $T_m$ measurements directly from PCR reactions which is impossible with other assays, such as TAQMAN, since TAQMAN probes are degraded during the PCR reaction.

Example 6

Figure 8:
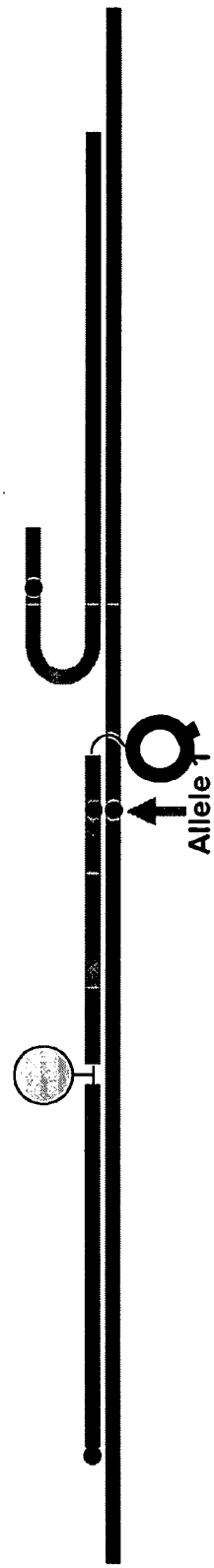
FIG. 8 schematically illustrates the Specimer™ "Molecular Switch" in a tandem switch competition platform.
Figure 8:
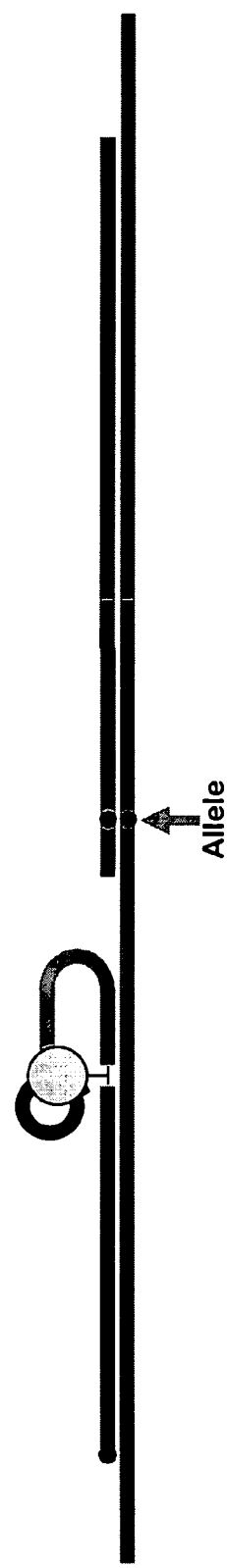
Figure 9:
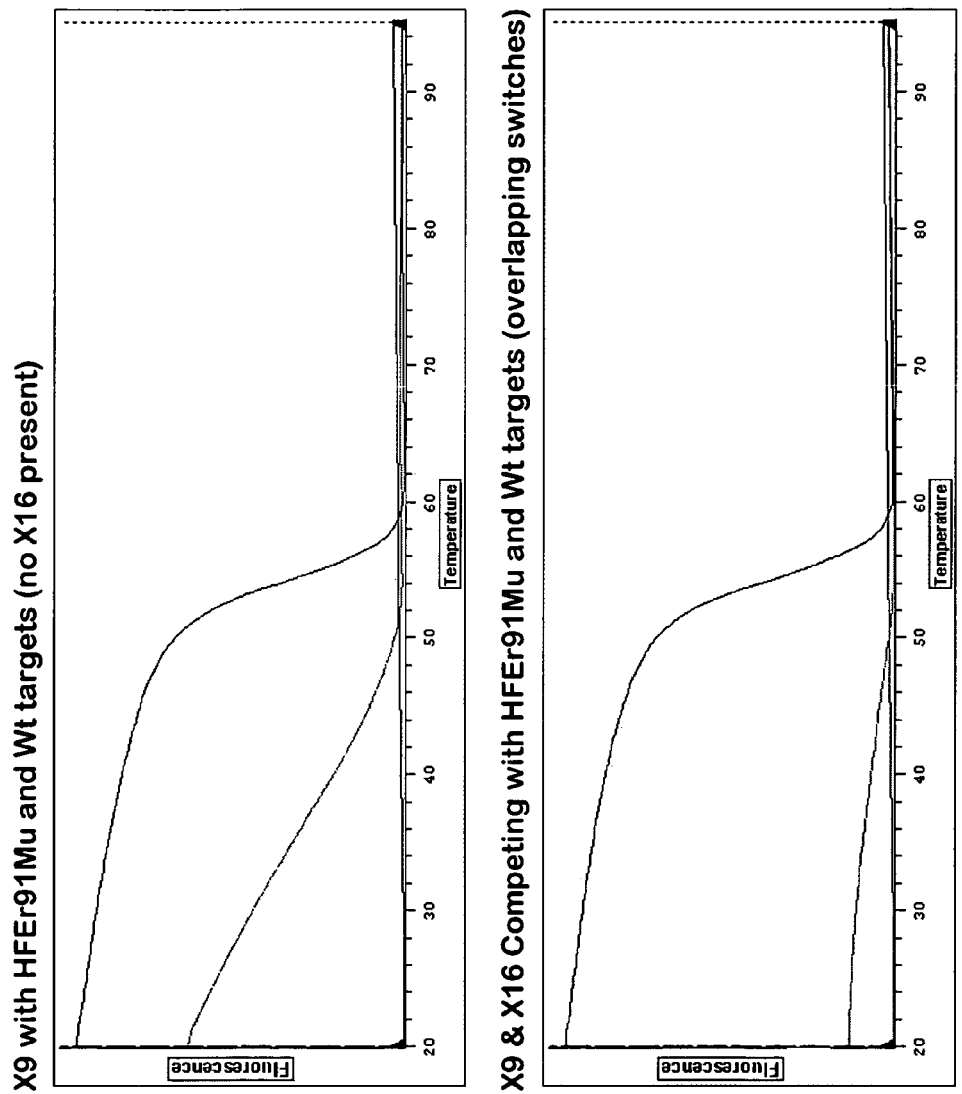
FIG. 9 depicts the results of melting curves (as measured by fluorescence) using Specimer™ Hemochromatosis probes X9WtH63D (SEQ ID NO:9) and X16WtH63D (SEQ ID NO:16) and targets HFEr91Mu (SEQ ID NO:22) and HFEr91Wt (SEQ ID NO:21) in a competing tandem switch formal which further enhances the switch effect.

To further test the utility of probes containing switch portions, probes which overlapped in their switch portions for a common target sequence were tested for their ability to further enhance mismatch discrimination over a very broad temperature range. The buffer and assay conditions were the same as those described in EXAMPLE 2 exception that the final probe and target concentrations were 2 µM X9 (SEQ ID NO:9), 3 µM HFEr91Wt (SEQ ID NO:21) or HFEr91Mu (SEQ ID NO:22), and either no X16 (SEQ ID NO:16) or 6 µM X16. In this example the X16 probe was designed to overlap in its switch portion with the switch portion of the X9 probe when they were both hybridized to a common target. The concept was to design the competing switch portion of the X16 probe (unlabeled) and the X9 probe (labeled) such that they would compete for hybridization of a common sequence in the target. See FIG. 8 for an illustration of this concept. Additionally, the X9 was designed to be completely complimentary in its switch portion to the HFEr91 Wt (wildtype) target, while the switch portion of the X16 probe is complimentary to the HFEr91 Mu (mismatch) target. In this "dueling" switch approach the X16 probe further displaces the switch portion of the X9 probe away from the mismatch target, while it has little effect (since it has a mismatch) with the wild-type target. FIG. 9 clearly shows the benefit of this approach since in the presence of the X16 probe discrimination of the X9 probe for match verses mismatch targets is increased approximately four-fold and shows very good mismatch discrimination over a temperature range of approximately 30° C.

In an alternative switch competition assay format, the molecular switch may be used to displace a competing adjacent labeled probe. If the switch is closed, the labeled probe is displaced; if the switch is open, the label is not displaced. This provides enhanced discrimination with any detectable label.

While preferred embodiments and methods have been shown and described, it will be apparent to one of ordinary skill in the art that numerous alterations may be made without departing from the spirit or scope of the invention. Therefore, the invention is not limited except in accordance with the following claims.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

What is claimed is:

1. A tripartite oligonucleotide consisting essentially of the following three components:
   (a) a nucleic acid anchor region complementary to a first sequence of nucleic acid residues of a target nucleic acid; and
   (b) a bridging domain; and
   (c) a binding domain,
   wherein said bridging domain and said binding domain form a switch domain,
   wherein said binding domain comprises 2-20 nucleic acid bases or analogs thereof complementary to said target nucleic acid and said binding domain has less affinity for said target nucleic acid than said anchor region,
   wherein said bridging domain is located between said anchor region and said binding domain and comprises 2-11 universal, generic or mismatched natural bases or analogs thereof or a mixture of universal and non-hydrogen bonding natural bases that do not form a Watson-Crick hybridization complex with said target nucleic acid, wherein two or more universal or non-hydrogen bonding natural bases or analogs thereof or a mixture of universal and non-hydrogen bonding natural bases in said bridging domain are juxtaposed, and wherein said universal or non-hydrogen bonding natural bases in said bridging domain substitute for bases complementary to nucleotide bases of said target nucleic acid and enhance sensitivity to the presence of a mismatch between the binding region of the switch domain and the target sequence,
   wherein said switch domain is able to discriminate between (i) a sequence of nucleic acid residues of said target nucleic acid that is complementary to said binding domain and (ii) a second mismatch sequence of nucleic acid residues of said target nucleic acid that contains at least one nucleic acid residue that is not complementary to said binding domain; under conditions wherein said anchor region (a) forms a stable duplex with said first sequence of nucleic acid residues of said target nucleic acid; and
   wherein said target nucleic acid comprises one or more sequences selected from the group consisting of a sequence that is associated with a disease or condition, a sequence that is associated with an infectious organism, and a sequence comprising a genetic variation.

2. An oligonucleotide according to claim 1, further comprising at least one detectable label.

3. An oligonucleotide according to claim 2, wherein the amount of signal detected from said detectable label is determinative of the hybridization status of said switch domain.

4. An oligonucleotide according to claim 2, wherein said at least one detectable label is a fluorescent label.

5. An oligonucleotide according to claim 4, further comprising a quencher, wherein said quencher and said fluorescent label interact to modulate the amount of signal detected from said fluorescent label.

6. An oligonucleotide according to claim 2, further comprising a quencher and a second fluorescent label, wherein the amount of signal detected from said second fluorescent label is determinative of the hybridization status of said region (a).

7. An oligonucleotide according to claim 3, wherein the amount of signal detected from said at least one detectable label is decreased when the switch domain is not hybridized to said target nucleic acid, relative to the amount of signal detected from said at least one detectable label when the switch domain is hybridized to said target nucleic acid.

8. An oligonucleotide according to claim 2, wherein said at least one detectable label is a first fluorescent label and a second fluorescent label, wherein said first and said second fluorescent labels interact to modulate the amount of signal detected from said first and/or said second fluorescent label dependent on the hybridization status of said switch domain.

9. A tripartite oligonucleotide consisting essentially of the following three components:
   (a) a nucleic acid anchor region complementary to a first sequence of nucleic acid residues of a double-stranded target nucleic acid, and
   (b) a bridging domain; and
   (c) a binding domain,
   wherein said bridging domain and said binding domain form a switch domain,
   wherein said binding domain comprises 2-20 nucleic acid bases or analogs thereof fully complementary to a second sequence of said double stranded target nucleic acid, and wherein said binding domain has less affinity for the target sequence than said anchor region,
   wherein said bridging domain is located between said anchor region and said binding domain and comprises 2-11 universal, generic or mismatched natural bases or analogs thereof or a mixture of universal bases and non-hydrogen bonding natural bases that do not form a Watson-Crick hybridization complex with said target nucleic acid, wherein two or more universal or non-hydrogen bonding bases or analogs thereof or a mixture of universal and non-hydrogen bonding natural bases or analogs thereof or a mixture of universal and non-hydrogen bonding natural bases in said bridging domain are juxtaposed, and wherein said universal or non-hydrogen bonding natural bases in said bridging domain substitute for bases complementary to nucleotide bases of said target nucleic acid and enhance sensitivity to the presence of a mismatch between the binding region of the switch domain and the target sequence;
   wherein said switch domain is able to discriminate between (i) a sequence of nucleic acid residues of said double-stranded target nucleic acid that is complementary to said binding domain and (ii) a second mismatch sequence of nucleic acid residues of said double-stranded target nucleic acid that contains at least one nucleic acid residue that is not complementary to said binding domain; under conditions wherein said anchor region (a) forms a stable triple-stranded nucleic acid with said first sequence of nucleic acid residues of said double-stranded target nucleic acid; and
   wherein said target nucleic acid comprises one or more sequences selected from the group consisting of a sequence that is associated with a disease or condition, a sequence that is associated with an infectious organism, and a sequence comprising a genetic variation.

10. A tandem oligonucleotide assembly comprising at least two oligonucleotides according to claim 1.

11. A tandem oligonucleotide assembly according to claim 10, further comprising a first detectable label associated with a first oligonucleotide and a second detectable label associated with a second oligonucleotide, wherein the amount of signal detected from said first and/or said second detectable label is altered when said tandem oligonucleotide assembly is hybridized to a target nucleic acid, relative to the amount of signal detected from said first and/or said second detectable label detected when either oligonucleotide is hybridized to said target nucleic acid individually.

12. A tandem oligonucleotide assembly according to claim 11, wherein said first and said second detectable labels are both fluorescent labels, further wherein said first fluorescent label transfers energy non-radiatively to said second fluorescent label when said first and said second oligonucleotides are both hybridized to said target nucleic acid.

13. A tandem oligonucleotide assembly according to claim 10, wherein the binding domains of said first oligonucleotide and said second oligonucleotide hybridize at least in part with overlapping regions of the target nucleic acid.

14. A tandem oligonucleotide assembly according to claim 10, wherein said first oligonucleotide is attached to a solid support.

15. An oligonucleotide according to claim 1, further comprising a 5' modification, wherein said modified oligonucleotide is resistant to digestion by enzymes possessing 5' nuclease activity.

16. An oligonucleotide according to claim 1, wherein said region (a) is 15-150 nucleotides in length.

17. An oligonucleotide according to claim 1, wherein said oligonucleotide suitable for use as a primer in an enzymatic reaction, and wherein the switch domain is positioned on the 3' terminus such that the oligonucleotide does not support 3' extension when the binding domain of said switch domain is not complementary to the target nucleic acid, but does support extension when the binding domain of said switch domain is complementary to the target nucleic acid.

18. An oligonucleotide comprising:
   (a) a nucleic acid anchor region complementary to a first sequence of nucleic acid residues of a target nucleic acid; and
   (b) a switch domain comprising at least one bridging domain and at least one binding domain, wherein said binding domain comprises 2-20 nucleic acid bases or analogs thereof complementary to said target nucleic acid and said binding domain has less affinity for said target nucleic acid than said anchor region,
   wherein said bridging domain is located between said anchor region and said binding domain and comprises 2-11 universal, generic or mismatched natural bases or analogs thereof or a mixture of universal and non-hydrogen bonding natural bases that do not form a Watson-Crick hybridization complex with said target nucleic acid, wherein two or more universal or non-hydrogen bonding natural bases or analogs thereof or a mixture of universal and non-hydrogen bonding natural bases in said bridging domain are juxtaposed, and wherein said universal or non-hydrogen bonding natural bases in said bridging domain substitute for bases complementary to nucleotide bases of said target nucleic acid and enhance sensitivity to the presence of a mismatch between the binding region of the switch domain and the target sequence,
   wherein said switch domain is able to discriminate between (i) a sequence of nucleic acid residues of said target nucleic acid that is complementary to said binding domain and (ii) a second mismatch sequence of nucleic acid residues of said target nucleic acid that contains at least one nucleic acid residue that is not complementary to said binding domain; under conditions wherein said anchor region (a) forms a stable duplex with said first sequence of nucleic acid residues of said target nucleic acid; and wherein said tar et nucleic acid comprises one or more sequences selected from the group consisting of a sequence that is associated with a disease or condition, a sequence that is associated with an infectious organism, and a sequence comprising a genetic variation, wherein said oligonucleotide is attached to an electron conducting solid surface, and wherein the amount of hybridization to said target nucleic acid controls the amount of current flow.

19. The oligonucleotide of claim 1, wherein said target nucleic acid comprises a sequence that is associated with a disease or condition.

20. The oligonucleotide of claim 1, wherein said target nucleic acid comprises a sequence that is associated with an infectious organism.

21. The oligonucleotide of claim 1, wherein said target nucleic acid comprises a sequence comprising a genetic variation.

22. The oligonucleotide of claim 1, wherein said target nucleic acid comprises a sequence comprising a human genetic variation.

23. The oligonucleotide of claim 1, wherein said target nucleic acid comprises a sequence corresponding to human DNA.

24. The oligonucleotide of claim 1, wherein said at least one nucleic acid residue of said target nucleic acid that is not complimentary to said binding domain is a human genetic variation.

25. The oligonucleotide of claim 1, wherein said at least one nucleic acid residue of said target nucleic acid that is not complimentary to said binding domain is a human mutation.

26. The oligonucleotide of claim 1, wherein said at least one nucleic acid residue of said target nucleic acid that is not complimentary to said binding domain is associated with a disease or condition.

27. The oligonucleotide of claim 1, wherein said at least one nucleic acid residue of said target nucleic acid that is not complimentary to said binding domain is a single nucleotide polymorphism (SNP).

28. The oligonucleotide of claim 1, wherein said switch domain is able to discriminate between (a) a target nucleic acid comprising a sequence associated with a disease or condition; and (b) a target nucleic acid that does not comprise said sequence associated with said disease or condition.

29. The oligonucleotide of claim 1, wherein said switch domain is able to discriminate between (a) a target nucleic acid comprising a single nucleotide polymorphism; and (b) a target nucleic acid that does not comprise said single nucleotide polymorphism.

30. The oligonucleotide of claim 1, wherein said switch domain is able to discriminate between (a) a target nucleic acid comprising a sequence associated with an infectious organism; and (b) a target nucleic acid that does not comprise said sequence associated with said infectious organism.

31. The oligonucleotide of claim 1, wherein said bridging domain comprises universal or generic bases.

32. The oligonucleotide of claim 1, wherein said bridging domain comprises generic bases.

33. The oligonucleotide of claim 1, wherein said bridging domain comprises universal bases.

34. The oligonucleotide of claim 1, wherein said bridging domain comprises at least two juxtaposed universal bases.

35. The oligonucleotide of claim 1, wherein said anchor region is at the 5'-end of said bridging domain, and wherein said binding domain is at the 3'-end of said bridging domain.

36. The oligonucleotide of claim 9, wherein said anchor region is at the 5'-end of said bridging domain, and wherein said binding domain is at the 3'-end of said bridging domain.

* * * * *

SEQUENCE LISTING

```
<160> NUMBER OF SEQ ID NOS: 24

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (18)..(22)
<223> OTHER INFORMATION: universal base; see specification as filed for
      detailed description of substitutions
<220> FEATURE:
<223> OTHER INFORMATION: see specification as filed for detailed
      description of labels and terminal modifications

<400> SEQUENCE: 1
ugaccagctg ttcgtgtnnn nngatcatg                                      29

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (18)..(22)
<223> OTHER INFORMATION: universal base; see specification as filed for
      detailed description of substitutions
<220> FEATURE:
<223> OTHER INFORMATION: see specification as filed for detailed
      description of labels and terminal modifications

<400> SEQUENCE: 2
tgaccagctg ttcgtgtnnn nngatcatg                                      29

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (20)..(23)
<223> OTHER INFORMATION: universal base; see specification as filed for
      detailed description of substitutions
<220> FEATURE:
<223> OTHER INFORMATION: see specification as filed for detailed
      description of labels and terminal modifications

<400> SEQUENCE: 3
ugaccagctg ttcgtgttcn nnnatcatga g                                   31
```

```
<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (18)..(22)
<223> OTHER INFORMATION: universal base; see specification as filed for
      detailed description of substitutions
<220> FEATURE:
<223> OTHER INFORMATION: see specification as filed for detailed
      description of labels and terminal modifications

<400> SEQUENCE: 4
tgaccagctg ttcgtgtnnn nngatcat                                            28

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (18)..(23)
<223> OTHER INFORMATION: universal base; see specification as filed for
      detailed description of substitutions
<220> FEATURE:
<223> OTHER INFORMATION: see specification as filed for detailed
      description of labels and terminal modifications

<400> SEQUENCE: 5
tgaccagctg ttcgtgtnnn nnnatcat                                            28

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (18)..(23)
<223> OTHER INFORMATION: universal base; see specification as filed for
      detailed description of substitutions
<220> FEATURE:
<223> OTHER INFORMATION: see specification as filed for detailed
      description of labels and terminal modifications

<400> SEQUENCE: 6
tgaccagctg ttcgtgtnnn nnnatcat                                            28

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (17)..(18)
<223> OTHER INFORMATION: S18 spacer present
<220> FEATURE:
<223> OTHER INFORMATION: see specification as filed for detailed
      description of labels and terminal modifications
```

-continued

```
<400> SEQUENCE: 7
tgaccagctg ttcgtgtatc at                                            22

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (15)..(19)
<223> OTHER INFORMATION: universal base; see specification as filed for
      detailed description of substitutions
<220> FEATURE:
<223> OTHER INFORMATION: see specification as filed for detailed
      description of labels and terminal modifications

<400> SEQUENCE: 8
ccagctgttc gtgtnnnnng atcat                                         25

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (18)..(22)
<223> OTHER INFORMATION: universal base; see specification as filed for
      detailed description of substitutions
<220> FEATURE:
<223> OTHER INFORMATION: see specification as filed for detailed
      description of labels and terminal modifications

<400> SEQUENCE: 9
tgaccagctg ttcgtgtnnn nngatcatg                                     29

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (19)..(23)
<223> OTHER INFORMATION: universal base; see specification as filed for
      detailed description of substitutions
<220> FEATURE:
<223> OTHER INFORMATION: see specification as filed for detailed
      description of labels and terminal modifications

<400> SEQUENCE: 10
atgaccagct gttcgtgtnn nnngatcat                                     29

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (18)..(21)
<223> OTHER INFORMATION: universal base; see specification as filed for
      detailed description of substitutions
```

```
-continued

<220> FEATURE:
<223> OTHER INFORMATION: see specification as filed for detailed
      description of labels and terminal modifications

<400> SEQUENCE: 11
tgaccagctg ttcgtgtnnn ntgatcatga g                                  31

<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tggatgacca gctgttcgtg ttctatgatc atgagagt                           38

<210> SEQ ID NO 13
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
actctcatga tcatagaaca cgaacagctg gtcatcca                           38

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (16)..(19)
<223> OTHER INFORMATION: universal base; see specification as filed for
      detailed description of substitutions
<220> FEATURE:
<223> OTHER INFORMATION: see specification as filed for detailed
      description of labels and terminal modifications

<400> SEQUENCE: 14
gatccagctg ttcgtnnnnt atgatcatga ga                                 32

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (16)..(19)
<223> OTHER INFORMATION: universal base; see specification as filed for
      detailed description of substitutions
<220> FEATURE:
<223> OTHER INFORMATION: see specification as filed for detailed
      description of labels and terminal modifications

<400> SEQUENCE: 15
gatccagctg ttcgtnnnnt atgatgatga ga                                 32

<210> SEQ ID NO 16
<211> LENGTH: 32
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (8)..(12)
<223> OTHER INFORMATION: universal base; see specification as filed for
      detailed description of substitutions

<400> SEQUENCE: 16
gatgatgnnn nntcgccgtg tggagccccg aa                                    32

<210> SEQ ID NO 17
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tggatgacca gctgttcgtg ttctatgatg atgagagt                              38

<210> SEQ ID NO 18
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
actctcatca tcatagaaca cgaacagctg gtcatcca                              38

<210> SEQ ID NO 19
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cacggcgact ctcatgatca tagaacacga acagctggtc atccacgta                  49

<210> SEQ ID NO 20
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cacggcgact ctcatcatca tagaacacga acagctggtc atccacgta                  49

<210> SEQ ID NO 21
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
agccacatct ggcttgaaat tctactggaa acccatggag ttcggggctc cacacggcga      60
ctctcatgat catagaacac gaacagctgg tca                                   93
```

```
<210> SEQ ID NO 22
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
agccacatct ggcttgaaat tctactggaa acccatggag ttcggggctc cacacggcga        60
ctctcatcat catagaacac gaacagctgg tca                                    93

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cctggtcttt ccttgtttga ag                                                22

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
acatctggct tgaaattcta ct                                                22
```